US009034584B2

(12) United States Patent
Kattman et al.

(10) Patent No.: US 9,034,584 B2
(45) Date of Patent: May 19, 2015

(54) METABOLIC MATURATION IN STEM CELL-DERIVED TISSUE CELLS

(75) Inventors: Steven Kattman, Madison, WI (US); Chad Koonce, Madison, WI (US); Natsuyo Aoyama, Madison, WI (US); Jennifer Luebke-Wheeler, Baraboo, WI (US); Brad Swanson, Waunakee, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 0 days.

(21) Appl. No.: 13/560,159

(22) Filed: Jul. 27, 2012

(65) Prior Publication Data

US 2013/0029368 A1 Jan. 31, 2013

Related U.S. Application Data

(60) Provisional application No. 61/513,164, filed on Jul. 29, 2011.

(51) Int. Cl.
*G01N 33/567* (2006.01)
*C12Q 1/00* (2006.01)
*C12N 5/077* (2010.01)

(52) U.S. Cl.
CPC .......... *C12N 5/0657* (2013.01); *C12N 2500/25* (2013.01); *C12N 2500/32* (2013.01); *C12N 2500/33* (2013.01); *C12N 2500/36* (2013.01); *C12N 2500/99* (2013.01)

(58) Field of Classification Search
USPC .................................................. 435/4, 7.21
See application file for complete search history.

(56) References Cited

U.S. PATENT DOCUMENTS

| 7,875,453 B2 | 1/2011 | Collins .......................... 435/377 |
| 7,932,084 B2 | 4/2011 | Katz et al. ...................... 435/325 |
| 2006/0057124 A1 | 3/2006 | Shim et al. .................... 424/93.7 |
| 2010/0081200 A1 | 4/2010 | Rajala et al. ................... 435/377 |
| 2010/0143313 A1 | 6/2010 | Yarmush et al. .............. 424/93.7 |
| 2010/0317104 A1 | 12/2010 | Elefany et al. ................ 435/366 |

FOREIGN PATENT DOCUMENTS

| WO | WO 00/27996 | | 5/2000 | |
| WO | WO 2008/112323 | * | 9/2008 | ............... C12N 5/06 |
| WO | WO 2009/055818 | | 4/2009 | |
| WO | WO 2009/117098 | | 9/2009 | |
| WO | WO 2010/093655 | | 8/2010 | |

OTHER PUBLICATIONS

Noll et al. (1992, Am. J. Physiol., vol. 262, pp. C1297-C1303).*
Carley et al. (2011, J. Biological Chem., vol. 286(6), pp. 4589-4597).*
Khodadadi et al. (2008, Archives of Iranian Med., vol. 11(1), pp. 42-49).*
Bordoni et al. (2005, Nutrition, Metabolism and Cardiovascular Dis., vol. 15, pp. 166-173).*
Vidarsson et al. (2010, Stem Cell Rev. And Rep., vol. 6, pp. 108-120).*
Wheeler et al. (2007, Pediatric Critical Care Med., Springer-Verlag London, pp. 742-743).*
Cheng, et al., "Cardiomyocyte-restricted peroxisome proliferator-activated receptor-delta deletion perturbs myocardial fatty acid oxidation and leads to cardiomyopathy," *Nat. Med.*, 10:1245-50, 2004.
Chung, et al., "Glycolytic network restricting integral to the energetics of embryonic stem cell cardiac differentiation," *J. Mol. Cell. Cardio.*, 48:725-34, 2010.
Chung, et al., "Mitochondrial oxidative metabolism is required for the cardiac differentiation of stem cells," *Nat. Clin. Pract. Cardiovasc. Med.*, 4:S60-S67, 2007.
Fischer, et al., "Changes in creatine transporter function during cardiac maturation in the rat," *BMC Develop. Biol.*, 10:70, 2010.
He, et al., "Human embryonic stem cells develop into multiple types of cardiac myocytes: action potential characterization," *Circ. Res.*, 93:32-39, 2003.
International Search Report and Written Opinion issued in Application No. PCT/US2012/048653, dated Jan. 4, 2013.
Lehman and Kelly, "Transcriptional activation of energy metabolic switches in the developing and hypertrophied heart," *Clin. Exp. Pharmacol. Physiol.*, 29:339-45, 2002.
Lopaschuk and Jaswal, "Energy metabolic phenotype of the cardiomyocyte during development, differentiation, and postnatal maturation," *J. Cardio. Pharmacol.*, 56:130-140, 2010.
Sharma, et al., "Murine embryonic stem cell-derived hepatic progenitor cells engraft in recipient livers with limited capacity of liver tissue formation," *Cell Transplant.*, 17:313-23, 2008.
Vidarsson, et al., "Differentiation of human embryonic stem cells to cardiomyocytes for in vitro and in vivo applications," *Stem Cell Rev. and Rep.*, 6:108-120, 2010.

\* cited by examiner

*Primary Examiner* — Anoop Singh
*Assistant Examiner* — David A Montanari
(74) *Attorney, Agent, or Firm* — Parker Highlander PLLC

(57) ABSTRACT

The present invention concerns methods and compositions for promoting a conversion in stem cells or cells derived therefrom from glycolysis to aerobic respiration and its associated pathways, including oxidative phosphorylation, the TCA cycle, fatty acid oxidation, and pyruvate decarboxylation, for example. In specific embodiments, certain media is employed to improve metabolic maturation of particular stem cell-derived cells, including human embryonic stem cells and human induced pluripotent stem cells, for example. Particular media comprises media without glucose or optionally without pyruvate, with fatty acids, with L-carnitine, with taurine, creatine, non-essential amino acids, L-glutamine, and with anti-oxidants or free-radical scavengers, for example.

24 Claims, 7 Drawing Sheets

METABOLIC MATURATION IN STEM CELL-DERIVED TISSUE CELLS

This application claims the benefit of U.S. Provisional Patent Application No. 61/513,164, filed Jul. 29, 2011, which is incorporated herein by reference in its entirety.

BACKGROUND OF THE INVENTION

1. Field of the Invention

The present invention generally concerns the fields of cell biology and molecular biology. In specific cases, the invention concerns the field of stem cell biology and maturation of stem cell-derived cells, including cardiomyocytes and hepatocytes, for example.

2. Description of Related Art

During fetal stages, tissues primarily utilize glycolysis as the primary energy source for metabolism (Lehman and Kelly, 2002; Lopaschuk et al., 2010). During perinatal development of many tissues, including heart and liver, the primary form of metabolism switches to fatty acid oxidation (FAO), which then provides an intermediate for the citric acid cycle (TCA cycle). The majority of media is designed for immortalized, tumor-derived cell lines that are metabolically adapted to grow quickly and generate energy primarily through glycolysis with little reliance on aerobic respiration or mitochondria in general. Therefore, to improve the metabolic maturation state of human embryonic stem cell (hESC) and human induced pluripotent stem cell (hiPSC)-derived cell types, for example, it is necessary to promote aerobic respiration and its associated input pathways, as opposed to glycolysis.

SUMMARY OF THE INVENTION

The present invention is directed to methods and compositions related to increasing metabolic maturity of certain cell types, including, for example, cells derived from stem cells. In aspects of the invention, the methods concern affecting the cells to convert their primary form of metabolism from glycolysis to aerobic respiration. In particular embodiments of the invention, cells differentiated from stem cells exposed to methods of the present invention result in mature cells that have improved functional attributes. In specific cases of the invention, the metabolic maturity of cells derived from human embryonic stem cells or human induced pluripotent stem cells is enhanced.

Aspects of the present invention provides a cell culture system to enhance aerobic respiration and its associated pathways (including oxidative phosphorylation (OXPHOS), the TCA cycle, FAO, and pyruvate decarboxylation, for example) in cell types derived from hESCs or human induced pluripotent stem cells hiPSCs. Enhancing aerobic respiration via any or all of these pathways will improve the maturation state of the stem cell (SC)-derived cell types, thereby improving their functional attributes. For cardiomyocytes, this includes NPPA (ANP) and NPPB (BNP) inducibility.

In particular aspects of the invention, the metabolic maturity of cells derived from stem cells is improved by exposing the stem cell-derived cells to particular culture conditions. In specific embodiments of the invention, the cells are exposed to particular media that converts the primary form of metabolism away from glycolysis to aerobic respiration. The media may be of any kind to effect such a change, but in specific embodiments the media at least lacks serum and glucose, optionally lacks pyruvate, comprises one or more fatty acids, and may contain L-carnitine. For example, in some cases, the media comprises one or more fatty acids other than oleic acid. In particular cases, trace amounts of glucose may be present, for example less than 1 mg/mL. In certain cases, the media also comprises L-carnitine, creatine, taurine, non-essential amino acids, L-glutamine, beta-mercaptoethanol, ITS-A, or a combination thereof. In certain aspects, ascorbic acid may be included in the media. In some cases, the cells are genetically engineered to express regulatory genes that drive the expression of metabolic enzymes that function directly or indirectly in aerobic respiration pathways such as oxidative phosphorylation, the citric acid cycle, fatty acid oxidation, and/or pyruvate decarboxylation, for example. In some cases, the cells are genetically engineered to express genes that code for proteins that transport substrates utilized in aerobic respiration pathways (such as fatty acid transporters). In certain cases, the transporters include but are not limited to fatty acid translocase (Cd36); plasma membrane associated fatty acid binding protein; and/or fatty acid transport protein (FATP1-FATP6). Also, the cells may be genetically engineered to express anti-oxidants and/or free radical scavengers and/or the cell media may comprise anti-oxidants and free radical scavengers.

In still further aspects of the invention, the methods of the invention utilize particular media to evolve cells into a later stage of differentiation than if the cells had not been exposed to the particular media. In particular embodiments, stem cell-derived cells are grown in certain media to promote them to a later stage of differentiation, including a later stage of cardiomyocyte differentiation, for example. In specific cases, the cardiomyocytes are derived from embryonic stem cells or induced pluripotent stem cells, for example. In specific embodiments, cardiomyocytes are grown from induced pluripotent stem cells, human embryonic stem cells, or human induced pluripotent stem cells by increasing the fatty acid oxidation of the cells during incubation in particular media. In at least some cases, the resultant cardiomyocytes mature by decreasing the expression of "fetal" genes, such as NPPA, NPPB, smooth muscle actin and skeletal actin, and increasing adult genes/proteins, such as myosin light chain 2V, calsequestrin and ryanodine receptor.

In aspects of the invention, there are several ways to promote aerobic respiration and its associated pathways. For example, aerobic respiration may be promoted with the addition of L-carnitine (required for transport of fatty acids from the cytosol into the mitochondria), addition of fatty acids, removal of glucose, and the optional addition of pyruvate. Genetic engineering may also be employed to express regulatory genes that drive the expression of metabolic enzymes associated with the above mentioned metabolic pathways. A paradox to promoting aerobic respiration and oxidative phosphorylation in cells is the formation of free radicals, which can be detrimental to cellular viability. For this reason, embodiments of the invention include methodologies to provide anti-oxidants, such as ascorbic acid, to promote the cell viability and functional attributes. Overexpression of free-radical scavengers within the differentiated cells via genetic engineering may limit the detrimental effects of free radical toxicity in such cell culture systems.

In embodiments of the invention, the cells are genetically modified, for example to enhance expression of one or more aerobic respiration enzymes, enhance the availability of one or more aerobic respiration substrates, and/or to enhance expression of proteins that regulate or augment the function or expression of one or more aerobic respiration enzymes. The genetic modifications may utilize transgenically altered cells by expressing the genes under constitutive, tissue-specific, or chemically inducible promoters, for example. The genes may be provided to cells by a variety of vectors, including episomal, liposomal, plasmid, or viral vectors; they may also be provided by homologous recombination, transposons, or systems that allow removal of the transgene at a desired time, such as with a Cre-lox or similar system.

In aspects of the invention, there may be provided a method for testing the differentiation state of stem cell-derived cells in need of having metabolic maturity, comprising: a) contacting stem cell-derived cells with a medium that has one or more of the following characteristics: (i) is essentially free of serum; (ii) is essentially free of glucose and optionally essentially free of pyruvate; (iii) that comprises one or more fatty acids; (iv) that comprises L-carnitine; (v) that comprises creatine; (vi) that comprises taurine; (vii) that comprises non-essential amino acids; (viii) that comprises L-glutamine; (ix) that comprises beta-mercaptoethanol; and b) measuring the metabolic state of the cells. The metabolic state of the cells may be identified by gene expression or functional assay, at least in some cases. In specific embodiments for stem-cell derived cardiomyocytes, their lactate dehydrogenase activity is assayed. In specific embodiments for stem cell-derived cardiomyocytes, their response to endothelin (ET-1) as measured by BNP expression is assayed.

In still further aspects of the invention there is a composition comprising cells in need of metabolic maturity (for examples, stem cells or cells derived therefrom) and a medium comprising one or more of the following characteristics: (i) is essentially free of serum; (ii) is essentially free of glucose and optionally essentially free of pyruvate; (iii) that comprises one or more fatty acids; (iv) that comprises L-carnitine; (v) that comprises creatine; (vi) that comprises taurine; (vii) that comprises non-essential amino acids; (viii) that comprises L-glutamine; (ix) that comprises beta-mercaptoethanol; (x) that comprises ITS-A.

In particular embodiments, the stem cell-derived cells having metabolic maturity may be differentiated from a stem cell that could be a pluripotent stem cell or a tissue stem cell, such as a cardiac stem cell or a non-cardiac lineage stem cell or progenitor cell. In certain aspects, the cell is an oval/hepatoblast cell from a liver. The pluripotent stem cell may include an induced pluripotent stem cell, an embryonic stem cell, or a pluripotent stem cell derived by somatic cell nuclear transfer, for example.

In other aspects, the medium may be essentially free of glucose. For providing an energy source other than glucose, the medium may comprise a compound capable of forming a high energy phosphate bond, an acyl group carrier molecule, or a cardiomyocyte calcium channel modulator. For example, the medium may comprise creatine, carnitine, taurine, or a combination thereof. For providing a carbon and/or energy source other than glucose, the medium may comprise galactose, fructose, mannose, sucrose, maltose, lactose, trehalose, turanose, pyruvate, pyruvic acid, glutamine, glutamic acid, aspartate, aspartic acid, lactate, lactic acid, glycerol, or a combination thereof. In a particular aspect, the medium may comprise galactose. The galactose in the medium may be at least or about 1, 2, 3, 4, 5, 6, 7, 8, 9, 10, 15, 20, 25, 50 mM or any range derivable therein. The medium may also comprise pyruvate or pyruvic acid. The pyruvate or pyruvic acid in the medium may be at least or about 0.01, 0.05, 0.1, 0.5, 1, 2, 3, 4, 5, 6, 7, 8, 9, 10 mM or any range derivable therein.

In certain cases of the invention, stem cells are differentiated into cardiomyocytes. In specific embodiments, cardiomyocytes are generated from hESCs or hiPSCs, for example, using certain media of the invention that promotes aerobic respiration in the cells. It is beneficial to have cardiomyocytes having metabolic maturity at least to reduce the 'fetal' or basal 'stressed' or 'hypertrophic' state and to promote reliance on mitochondria, for example to help in cardiotoxicity assays and/or hypertrophy assays.

In still other aspects of the invention, stem cells are differentiated into hepatocytes. In specific embodiments, hepatocytes are generated from hESCs or hiPSCs, for example, using certain media of the invention that promotes aerobic respiration in the cells. It is beneficial to have hepatocytes having metabolic maturity, for example in cases where stem cell-derived hepatocytes have sufficient numbers of ATP-rich mitochondria capable of oxidative phosphorylation; such a state of metabolism reduces the likelihood of reduced oxidative phosphorylation or ATP levels that can result from toxic intermediates upon exposure of the hepatocytes to certain drugs.

In certain embodiments of the invention, there is a defined media that is essentially glucose-free, essentially serum-free, and which comprises one or more fatty acids. In some aspects, the defined media has one or more of the following characteristics: a) creatine; b) optionally, pyruvate; c) L-carnitine; d) taurine; e) L-glutamine; f) beta-mercaptoethanol; g) ITS-A; and h) non-essential amino acids, for example.

Kits housing the media of the invention or one or more components thereof are encompassed in the invention.

In some embodiments of the invention, there is a method of improving the metabolic maturity state of stem cell-derived cells, comprising the step of exposing the stem cell-derived cells to conditions to convert the metabolism of the cells from glycolysis to aerobic respiration, to thereby improve the metabolic maturity state of the cells. In at least some cases, the exposing step is further defined as culturing the cells in a defined media that is essentially glucose-free, essentially serum-free, and which comprises one or more fatty acids. In specific embodiments, the defined media has one or more of the following characteristics: a) creatine; b) optionally, pyruvate; c) L-carnitine; d) taurine; e) L-glutamine; f) beta-mercaptoethanol; g) ITS-A; and h) non-essential amino acids.

In some embodiments, the media further comprises one or more anti-oxidants, such as one selected from the group consisting of vitamin A (such as beta-carotene), vitamins C (such as ascorbic acid) and E, selenium, melatonin, carnosine, rhodiaola, luteolin, wheat sprout enzymes, coenzyme Q, and linoleic acid. In some aspects, the media further comprises one or more free radical scavengers, such as one selected from the group consisting of ascorbic acid, vitamin E, and β-carotene.

In certain aspects, the stem cell-derived cells are hepatocytes or cardiomyocytes, and in some cases the cells are genetically modified. Genetic modification of the cells includes modification to enhance expression of one or more aerobic respiration enzymes, enhance the availability of one or more aerobic respiration substrates, and/or to enhance expression of proteins that regulate or augment the function or expression of one or more aerobic respiration enzymes. Exemplary aerobic respiration-related enzymes include one or more selected from the group consisting of fatty acid translocase (Cd36), plasma membrane associated fatty acid binding protein, fatty acid transport protein (FATP1, FATP2, FATP3, FATP4, FATP5, and/or FATP6), acyl-CoA synthetase, carnitine palmitoyl transferase 1 (CPT1), carnitine palmitoyl transferase 2 (CPT2), peroxisome proliferator-activated receptor (PPAR) alpha, PPARbeta, and PPARdelta.

In some cases, the cells are genetically modified to express an enzyme selected from the group consisting of catalase, superoxide dismutase, peroxidase, methionine reductase, glutathione peroxidase, and a combination thereof. In specific cases, the exposing step is further defined as genetically modifying the stem cell-derived cells, such as to enhance expression of one or more aerobic respiration enzymes, one or more aerobic respiration substrates, and/or to enhance expression of proteins that regulate or augment the function or expression of one or more aerobic respiration enzymes.

The stem cell-derived cells may be cultured in the media for any suitable period of time to allow metabolic maturity, but in specific embodiments the timing is for at least two, three, four, five, six, seven, eight, nine, ten, or more days, for example.

In at least some embodiments, following the exposing step the method further comprises assaying the stem cell-derived cells for one or more characteristics, such as expression of one or more genes (for example, CPT1, PPARa, NPPA, and NPPB) or response in a cellular functional assay.

Although in particular embodiments the media matures stem cell-derived cells through utilization of aerobic respiration instead of glycolysis, in certain specific embodiments the maturation of the stem cell-derived stem cells occurs by other or additional mechanisms. In certain embodiments of the invention, there is a method of improving the metabolic maturity state of stem cell-derived cells, comprising the step of exposing the stem cell-derived cells to a defined media that is essentially glucose-free, essentially serum-free, and which comprises one or more fatty acids, to thereby improve the metabolic maturity state of the cells. In specific embodiments, the defined media has one or more of the following characteristics: a) creatine; b) optionally, pyruvate; c) L-carnitine; d) taurine; e) L-glutamine; f) beta-mercaptoethanol; g) ITS-A; and h) non-essential amino acids.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
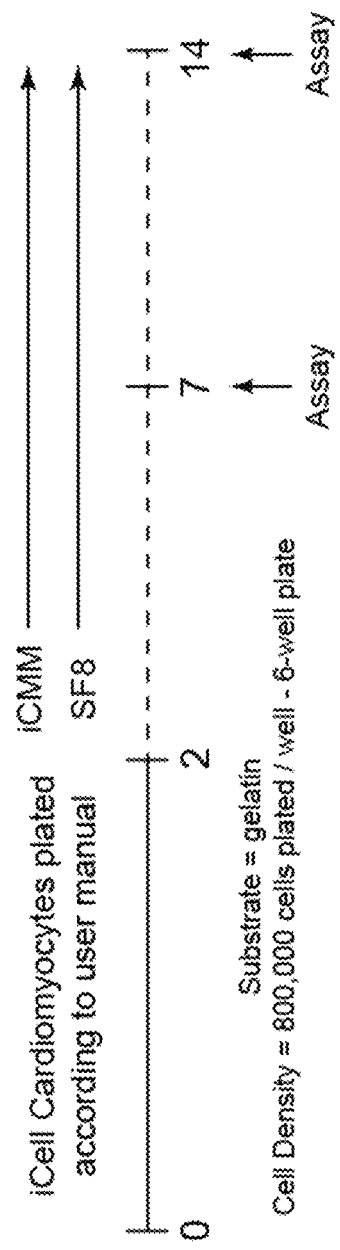
FIG. 1a-b: (a), A flow chart schematic of the cell culture studies with iPSC-derived cardiomyocytes (see Experiment 1, below). (b), iPSC-derived CMs cultured in SF8 upregulate CPT-1 and downregulated NPPB.

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein. Embodiments discussed in the context of methods and/or compositions of the invention may be employed with respect to any other method or composition described herein. Thus, an embodiment pertaining to one method or composition may be applied to other methods and compositions of the invention as well.

Throughout this application, the term "about" is used to indicate that a value includes the inherent variation of error for the device, the method being employed to determine the value, or the variation that exists among the study subjects.

"Cardiomyocytes" refers generally to any cardiomyocyte lineage cells, and can be taken to apply to cells at any stage of cardiomyocyte ontogeny without any restriction, unless otherwise specified. For example, cardiomyocytes may include both cardiomyocyte precursor cells and mature cardiomyocytes.

The term "cellular maturation" is a developmental process that is required for a cell to attain its fully functional state. ESC and iPSC-derived differentiated cells often exhibit a "fetal" state of development. Therefore, maturation of ESC and iPSC-derived tissues requires the loss of fetal gene/protein expression and associated functional characteristics, and the acquisition of gene expression and functional characteristics associated with adult or mature cells.

"Embryonic stem (ES) cells" are pluripotent stem cells derived from early embryos.

The term "essentially free" as used herein refers to a component in the media being present in no more than trace amounts, for example no more than 1 mg/mL glucose.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by introducing into or otherwise contacting the cell with reprogramming factors.

The terms "metabolic maturity" or "metabolic maturation" as used herein refers to the maturation of metabolic processes including, but not limited to, promotion in a cell of utilizing primarily fatty acid oxidation, citric acid cycle, and/or oxidative phosphorylation for metabolism in cells, as opposed to glycolysis. For example, fatty acid oxidation is readily utilized by adult cardiac tissue, but during development glycolysis is readily used by this tissue. The process of "maturing" stem cell-derived cells, such as iPS and ES cell-derived cardiomyocytes, promotes the use of these 'adult' metabolic pathways, in embodiments of the invention.

The term "primary form of metabolism" as used herein refers to the referenced metabolic pathway as being the primary source of metabolism. For example, fatty acid oxidation would be the primary form of metabolism if 80% of cellular metabolic energy was generated through fatty acid oxidation, 19% through glycolysis, and 1% through lactate oxidation.

"Pluripotency" refers to a stem cell that has the potential to differentiate into all cells constituting one or more tissues or organs, for example, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, descendants of totipotent cells or induced pluripotent stem cells.

The term "stem cell-derived cells" as used herein refer to any cell types generated from pluripotent stem cells by the process of differentiation.

A "gene," "polynucleotide," "coding region," "sequence," "segment," or "fragment," which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "transgene," or "exogenous" refers to a gene, nucleic acid, or polynucleotide which has been introduced into the cell or organism by artificial or natural means, such as an exogenous nucleic acid. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

I. Exemplary Media of the Invention and Use Thereof

In embodiments of the invention, cells are cultured in a medium that promotes the maturation state of the cell. In particular embodiments, the cells are stem cells or cells derived therefrom and the medium promotes aerobic respiration such that stem cell-derived tissue types have improved maturation states for the cells and improved functional attributes. In specific cases, particular pathways in the cells are affected to induce such a mature state, including, for example, oxidative phosphorylation, fatty acid oxidation, pyruvate decarboxylation, the Citric Acid Cycle, and their associated input pathways. In at least certain cases, the media promotes utilization of fatty acid metabolism as the primary form of metabolism, including to the diminution of the use of glycolysis. In at least some embodiments, glycolysis is no longer detectable.

Aspects of the invention include media comprising one or more of the following characteristics: (i) is essentially free of serum; (ii) is essentially free of glucose and optionally essentially free of pyruvate; (iii) that comprises one or more fatty acids; (iv) that comprises L-carnitine; (v) that comprises creatine; (vi) that comprises taurine; (vii) that comprises non-essential amino acids; (viii) that comprises L-glutamine; (ix) that comprises beta-mercaptoethanol; or (x) that comprises ITS-A.

In aspects of the invention the media comprises one or more fatty acids. The fatty acid(s) may be essential fatty acids (such as linoleic acid or alpha-linolenic acid), conditionally essential fatty acids, or a mixture of both. The fatty acid may be saturated or unsaturated (including cis or trans configuration). In some embodiments, the fatty acids have a chain of an even number of carbon atoms, including 4, 6, 8, 10, 12, 14, 16, 18, 20, 22, 24, 26, or 28, for example. The fatty acids may be short-chain fatty acids (SCFA) having tails of fewer than six carbons (i.e. butyric acid); medium-chain fatty acids (MCFA) having 6-12 carbons; long-chain fatty acids (LCFA) having tails longer than 12 carbons; very-long-chain fatty acids (VL-CFA) having tails longer than 22 carbons; or a mixture thereof. Examples of unsaturated fatty acids include myristoleic acid, palmitoleic acid, sapienic acid, oleic acid, edaic acid, vaccenic acid, linoleic acid, linoelaidic acid, α-linolenic acid, arachidonic acid, eicosapentaenoic acid, erucic acid, and docosahexaenoic acid. Examples of saturated fatty acids include lauric acid, myristic acid, palmitic acid, stearic acid, arachidic acid, behenic acid, lignoceric acid, and cerotic acid. The concentration of fatty acid(s) may be of any level so long as it promotes aerobic respiration in favor of glycolysis, but in specific embodiments the fatty acids are at 0.25×, 0.5×, 0.75×, 1×, 2×, 3×, 4×, 5×, 6×, 7×, 8×, 9×, or 10×, for example. In particular aspects the fatty acids are at a level between 0.25× and 5×, including between 0.25× and 2.5×, or between 0.5× and 1.5×, or between 0.75× and 1.25×, for example. (1×=0.02 mol each of linoleic and oleic acids per 0.01 mole of albumin.)

In specific cases, there is L-carnitine in the media, and the concentration may be of any kind so long as the media is capable of promoting aerobic respiration instead of glycolysis as a primary form of metabolism. The L-carnitine concentration may be 2 mM in specific cases, but in some cases the concentration is at least 0.25 mM, 0.5 mM, 0.75 mM, 1.0 mM, 1.25 mM, 1.5 mM, 1.75 mM, 2.25 mM, 2.5 mM, 2.75 mM, 3 mM, 3.5 mM, 4 mM, 4.5 mM, 5 mM, 7.5 mM, 10 mM, 12 mM, 15 mM, 20 mM, 25 mM, 30 mM, 35 mM, 40 mM, 45 mM, or 50 mM, for example. The L-carnitine concentration may be in a range between 0.25 mM and 50 mM, between 0.25 mM and 30 mM, between 0.25 mM and 25 mM, between 1 mM and 50 mM, between 1 mM and 30 mM, between 5 mM and 50 mM, between 5 mM and 30 mM, between 10 mM and 50 mM, between 10 mM and 30 mM, between 15 mM and 50 mM, between 15 mM and 30 mM, between 20 mM and 50 mM, between 20 mM and 30 mM, between 25 mM and 50 mM, between 25 mM and 30 mM, 0.25 mM and 10 mM, between 0.5 and 7.5 mM, between 0.75 and 5 mM, or between 1 and 3 mM, for example.

In certain aspects, there is creatine in the media, and the concentration may be of any kind so long as the media is capable of promoting aerobic respiration instead of glycolysis as a primary form of metabolism. The creatine concentration may be 5 mM in specific cases, but in some cases the concentration is 0.25 mM, 0.5 mM, 0.75 mM, 1.0 mM, 1.25 mM, 1.5 mM, 1.75 mM, 2.25 mM, 2.5 mM, 2.75 mM, 3 mM, 3.5 mM, 4 mM, 4.5 mM, 5 mM, 6 mM, 6.5 mM, 7 mM, 7.5 mM, 8 mM, 8.5 mM, 9 mM, 9.5 mM, or 10 mM, for example. The creatine concentration may be in a range between 0.25 mM and 10 mM, between 0.5 and 7.5 mM, between 2.5 and 7.5 mM, or between 3 and 6 mM, for example.

In further aspects, there is taurine in the media, and the concentration may be of any kind so long as the media is capable of promoting aerobic respiration instead of glycolysis as a primary form of metabolism. In some aspects, taurine is employed to prevent cardiomyocyte apoptosis. The taurine concentration may be 5 mM in specific cases, but in some cases the concentration is 0.25 mM, 0.5 mM, 0.75 mM, 1.0 mM, 1.25 mM, 1.5 mM, 1.75 mM, 2.25 mM, 2.5 mM, 2.75 mM, 3 mM, 3.5 mM, 4 mM, 4.5 mM, 5 mM, 6 mM, 6.5 mM, 7 mM, 7.5 mM, 8 mM, 8.5 mM, 9 mM, 9.5 mM, or 10 mM, for example. The creatine concentration may be in a range between 0.25 mM and 10 mM, between 0.5 and 7.5 mM, between 2.5 and 7.5 mM, or between 3 and 6 mM, for example.

In particular cases, there are non-essential amino acids in the media, and the concentration may be of any kind so long as the media is capable of promoting aerobic respiration instead of glycolysis as a primary form of metabolism. The non-essential amino acid concentration may be 1 mM in specific cases, but in some cases the concentration is 0.1 mM, 0.2 mM, 0.25 mM, 0.5 mM, 0.75 mM, 1.0 mM, 1.25 mM, 1.5 mM, 1.75 mM, 2.25 mM, 2.5 mM, 2.75 mM, 3 mM, 3.5 mM, 4 mM, 4.5 mM, 5 mM, 6 mM, 6.5 mM, 7 mM, 7.5 mM, 8 mM, 8.5 mM, 9 mM, 9.5 mM, or 10 mM, for example. The non-essential amino acid concentration may be in a range between 0.1 mM and 10 mM, between 0.1 and 7.5 mM, between 0.5 and 5 mM, between 0.5 and 2.5 mM, between 0.5 mM and 1 mM, or between 0.75 and 1.25 mM, for example.

In specific cases, there is L-glutamine in the media, and the concentration may be of any kind so long as the media is capable of promoting aerobic respiration instead of glycolysis as a primary form of metabolism. The L-glutamine concentration may be 2 mM in specific cases, but in some cases the concentration is 0.25 mM, 0.5 mM, 0.75 mM, 1.0 mM, 1.25 mM, 1.5 mM, 1.75 mM, 2.25 mM, 2.5 mM, 2.75 mM, 3 mM, 3.5 mM, 4 mM, 4.5 mM, 5 mM, 7.5 mM, or 10 mM, for example. The L-glutamine concentration may be in a range between 0.25 mM and 10 mM, between 0.5 and 7.5 mM, between 0.75 and 5 mM, or between 1 and 3 mM, for example.

In specific cases, there is beta-mercaptoethanol in the media, and the concentration may be of any kind so long as the media is capable of promoting aerobic respiration instead of glycolysis as a primary form of metabolism. The beta-mercaptoethanol concentration may be 2 mM in specific cases, but in some cases the concentration is 0.25 mM, 0.5 mM, 0.75 mM, 1.0 mM, 1.25 mM, 1.5 mM, 1.75 mM, 2.25 mM, 2.5 mM, 2.75 mM, 3 mM, 3.5 mM, 4 mM, 4.5 mM, 5 mM, 7.5 mM, or 10 mM, for example. The beta-mercaptoethanol concentration may be in a range between 0.25 mM and 10 mM, between 0.5 and 7.5 mM, between 0.75 and 5 mM, or between 1 and 3 mM, for example.

The concentration of ITS-A (Gibco cat #:51300-044: a combination of insulin, transferrin, and selenium in a phosphate buffered saline solution which also contains 11 g/L pyruvate in a 100× stock) may be of any level so long as it promotes aerobic respiration in favor of glycolysis, but in specific embodiments the fatty acids are at 0.25×, 0.5×, 0.75×, 1×, 2×, 3×, 4, 5×, 6×, 7×, 8×, 9×, or 10×, for example. In particular aspects the fatty acids are at a level between 0.25× and 5×, including between 0.25× and 2.5×, or between 0.5× and 1.5×, or between 0.75× and 1.25×, for example.

In some embodiments, the media comprises components that inhibit free radicals, such as those produced upon promotion of aerobic respiration and oxidative phosphorylation. Thus, in specific embodiments, the media comprises antioxidants and/or the cells are engineered to express antioxidants or the antioxidants are indirectly increased upon expression of another gene. Exemplary antioxidants include at least ascorbic acid, glutathione, Vitamin E, lipoic acid, uric acid, carotenes, ubiquinol, and α-tocopherol. Exemplary genes that encode antioxidants and for which the cells may be genetically altered to produce include catalase, superoxide dismutase, and/or peroxidase.

In certain aspects, the media comprises free-radical scavengers and/or the cells are engineered to express free radical scavengers directly or the free radical scavengers are indirectly increased upon expression of another gene. Exemplary free radical scavengers include at least ascorbic acid, vitamin E, and β-carotene.

In some embodiments, the cells are manipulated to harbor exogenous metabolic enzymes associated with such metabolic pathways as oxidative phosphorylation, fatty acid oxidation, pyruvate decarboxylation, and the Citric Acid Cycle. Exemplary fatty acid oxidation enzymes include acyl CoA dehydrogenase, enoyl CoA hydratase, L-β-hydroxyacyl CoA dehydrogenase, and β-ketothiolase; exemplary co-factors include flavin adenine dinucleotide (FAD) and nicotinamide adenine dinucleotide (NAD$^+$). Exemplary citric acid cycle enzymes include citrate synthase, aconitase, isocitrate dehydrogenase, α-ketoglutarate dehydrogenase, succinyl-CoA synthetase, succinate dehydrogenase, fumarase, and malate dehydrogenase, for example. Exemplary oxidative phosphorylation enzymes include NADH dehydrogenase, succinate dehydrogenase, electron transfer flavoprotein-ubiquinone oxidoreductase, Q-cytochrome c oxidoreductase, or cytochrome c oxidase, for example. Exemplary pyruvate decarboxylation enzymes include pyruvate dehydrogenase, dihydrolipoyl transacetylase, and dihydrolipoyl dehydrogenase, for example. Proteins or molecules that increase the concentration of fatty acids in cells or facilitate fatty acid transport into mitochondria include fatty acid translocase (Cd36); plasma membrane associated fatty acid binding protein; fatty acid transport protein (FATP1-FATP6); acyl-CoA synthetase; carnitine palmitoyl transferase 1 (CPT1); carnitine palmitoyl transferase 2 (CPT2); and/or L-carnitine. Transcription factors that activate genes implicated in metabolic maturation include peroxisome proliferator-activated receptors (PPARs) alpha, beta/delta.

In particular aspects of the invention, the media comprises one or more, including all, in some cases, of the following components or characteristics: no serum, no glucose, optionally pyruvate, L-carnitine, creatine, taurine, non-essential amino acids, L-glutamine, BME, ITS-A, linoleic acid, oleic acid, and antioxidants, such as ascorbic acid.

An exemplary specific media that may be employed in the invention includes one that comprises, consists of, or consists essentially of the following: Dulbecco's Modified Eagle Medium (DMEM; Invitrogen, Carlsbad, Calif.) having no glucose, no pyruvate); L-carnitine (2 mM); creatine (5 mM); taurine (5 mM); Non-Essential Amino Acids (1 mM) (for example, from Invitrogen); L-glutamine+BME (2 mM); ITS-A (1×); and linoleic-Oleic acid (1×: 0.02 mol each of linoleic and oleic acids per mole of albumin). Alternatively, L-glutamine without may be used and oleic acid may be omitted entirely.

Exemplary non-essential amino acids are commercially available and may include, for example, some or all of the following: alanine, arginine, aspartate, cysteine, glutamate, glutamine, glycine, proline, serine, taurine, histidine, glutathione threonine, and asparagine.

In embodiments of the invention, the medium comprises lipids, amino acids (including non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5 mM, but the concentration is particularly not limited thereto as long as it is appropriate for culturing the cell(s).

A culture vessel used for culturing the cells in the media can include, but is particularly not limited to the following: flask, flask for tissue culture, dish, petri dish, dish for tissue culture, multi dish, micro plate, micro-well plate, multi plate, multi-well plate, micro slide, chamber slide, tube, tray, CellSTACK® Chambers, culture bag, and roller bottle, as long as it is capable of culturing the cells therein. The cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, 2000 ml or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, laminin, and fibronectin and mixtures thereof, Matrigel™, and lysed cell membrane preparations (Klimanskaya et al., 2005).

Other culturing conditions can be appropriately defined. For example, the culturing temperature can be about 30 to 40° C., for example, at least or about 31, 32, 33, 34, 35, 36, 37, 38, 39° C. but particularly not limited to them. The $CO_2$ concentration can be about 1 to 10%, for example, about 2 to 5%, or any range derivable therein. The oxygen tension can be at least or about 1, 5, 8, 10, 20%, or any range derivable therein.

The length of incubation of the stem cell-derived cells may be of any length so long as it is sufficient to convert the cells' primary form of metabolism from glycolysis to aerobic respiration. In specific embodiments, the incubation occurs no less than about four days, for example. In specific embodiments, the media is exchanged for fresh media once or periodically.

II. Stem Cell-Derived Tissue Types

Embodiments of the invention include the enhancement of aerobic respiration in cells such that aerobic respiration, and not glycolysis, is the primary energy source for metabolism. Although the cells exposed to the media may be of any kind capable of developing into more mature cells as compared to growing the cells in another media, in specific embodiments the cells are stem-cell derived cells and tissue including, for example, stem cell-derived cardiomyocytes, hepatocytes, and pancreatic islet cells. Exemplary cells include human embryonic stem cells (hESCs), human induced pluripotent stem cells (hiPSCs), as well as hES cell or hiPS cell-derived cardiomyocytes, hepatocytes, and pancreatic islet cells.

III. Methods for Characterizing Metabolic Maturity

In embodiments of the invention, one can determine the metabolic maturity of cells, particularly following culturing methods of the present invention that promote aerobic respiration instead of glycolysis as the primary form of metabolism.

In aspects of the invention, the metabolic maturity is ascertained by one or more methods in the art that identify genotype, phenotype, morphology, gene expression, metabolic markers, cell surface markers, and/or cellular functional assay of the cell. In some embodiments of the invention, gene expression of one or more particular genes is identified following exposure of the cells to particular conditions, such as culturing in a particular medium of the invention. The gene and/or protein level and/or function may be ascertained, for example using northern, westerns, flow cytometry, ELISA, qPCR, and so forth. In specific embodiments, the genes encode proteins that are involved in a particular pathway associated with aerobic respiration and its associated pathways, including oxidative phosphorylation, the citric acid cycle (TCA), fatty acid oxidation, pyruvate decarboxylation, and the like. In specific embodiments, the genes may include CPT1 or PPARa (genes associated with fatty acid oxidation). In some cases, the genes encode proteins that signify development of a mature type of cell, such as hormone expression (such as decreased expression of NPPA/ANP and NPPB/BNP) and structural proteins associated with maturation (such as gain of myosin light chain 2V expression but loss of smooth muscle actin and skeletal actin expression). In specific aspects for mature or maturing cardiomyocytes, one can determine decreased expression of genes associated with a "fetal" state or cardiac hypertrophyic state such as, for example, NPPA (BNA) and NPPB (BNP).

Characterization of Cardiomyocytes

Cellular maturation is a developmental process that is required for a cell to attain its fully functional state. ESC and iPSC-derived differentiated cells often exhibit a "fetal" state of development. Therefore, maturation of ESC and iPSC-derived tissues requires the loss of fetal gene/protein expression and associated functional characteristics, and the acquisition of gene expression and functional characteristics associated with adult or mature cells. Many attributes of the cells can mature from the fetal state to the adult state, including: metabolism, cardiac hormones, structural/contractile properties and electrophysiology. Metabolic maturation refers specifically to the maturation of metabolic processes.

For cardiomyocytes, maturity can be assessed by the presence of decreased expression of genes associated with the a fetal state, such as NPPA, NPPB, smooth muscle actin and skeletal actin, and increasing expression of adult genes/proteins, such as myosin light chain 2V, calsequestrin and ryanodine receptor. Mature cells can be useful as a baseline state for studying cardiac hypertrophy by the reintroduction of a fetal gene program through the controlled addition of a hypertrophy inducing agonist such as endothelin 1. For example, the re-expression (or inducible expression) of the cardiac hormones NPPA (ANP) and NPPB (BNP) are characteristic of a hypertrophic response. Therefore, for ESC and iPSC derived cells to be useful in a cardiac hypertrophy assay, they need to be initially at a developmentally mature state with regard to these cardiac hormones so they can be converted under controlled conditions to a hypertrophic state, which is more similar to a "fetal" state. Measurement of the degree of inducibility of the hypertrophic state by the addition of an hypertrophy agonist (such as endothelin 1) is particularly useful as a screening assay for drug discovery for therapeutic agents effective against cardiac hypertrophy or for toxicity testing of drugs to assess off-target induction of cardiac hypertrophy.

Cardiomyocytes can be produced and characterized as described in U.S. Patent Application Publication No. 2011/0097799, incorporated by reference herein in its entirety. Cardiomyocytes can be purified or isolated, or alternatively, the purity of cardiomyocytes in a culture can be determined based on detection of cardiomyocytes in the culture. Cardiomyocytes derived from stem cells, such as induced pluripotent stem cells, have morphological characteristics of cardiomyocytes from other sources. They can be spindle, round, triangular or multi-angular shaped, and they may show striations characteristic of sarcomeric structures detectable by immunostaining. They may form flattened sheets of cells, or aggregates that stay attached to the substrate or float in suspension, showing typical sarcomeres and atrial granules when examined by electron microscopy.

For example, the purity of cardiomyocytes may be determined by detecting cardiomyocytes which express an exogenous marker gene under the control of a promoter of a cardiomyocyte-specific marker or which express an endogenous cardiomyocyte-specific marker. In a further aspect, such detection may be used to isolate or purify the cardiomyocytes for long-term storage in a medium described in certain aspects of the invention.

For example, the cardiomyocyte-specific markers may include: Cardiac troponin I (cTnI), a subunit of troponin complex that provides a calcium-sensitive molecular switch for the regulation of striated muscle contraction; Cardiac troponin T (cTnT); Nkx2.5, a cardiac transcription factor expressed in cardiac mesoderm during early mouse embryonic development, which persists in the developing heart; Atrial natriuretic factor (ANF, a hormone expressed in developing heart and fetal cardiomyocytes but down-regulated in adults; it is considered a good marker for cardiomyocytes because it is expressed in a highly specific manner in cardiac cells but not skeletal myocytes); Myosin heavy chain (MHC), particularly the β chain which is cardiac specific; Titin; tropomyosin; α-sarcomeric actinin; desmin; GATA-4 (a transcription factor that is highly expressed in cardiac mesoderm and persists in the developing heart; it regulates many cardiac genes and plays a role in cardiogenesis); MEF-2A, MEF-2B, MEF-2C, and/or MEF-2D (transcription factors that are expressed in cardiac mesoderm and persist in developing heart); N-cadherin, which mediates adhesion among cardiac cells; connexin 43, which forms the gap junction between cardiomyocytes; β1-adrenoceptor (β1-AR); creatine kinase MB (CK-MB) and/or myoglobin, which are elevated in serum following myocardial infarction; α-cardiac actin, early growth response-I; and/or cyclin D2.

Cardiomyocyte-specific markers can be detected using any suitable immunological technique, such as flow immunocytometry or affinity adsorption for cell-surface markers; immunocytochemistry (for example, of fixed cells or tissue sections) for intracellular or cell-surface markers; Western blot analysis of cellular extracts; and/or enzyme-linked immunoassay, for cellular extracts or products secreted into the medium. Antibodies that distinguish cardiac markers like cTnI and cTnT from other isoforms are available commercially from suppliers like Sigma-Aldrich (St. Louis, Mo.) and Spectral Diagnostics (Toronto, Ontario). Expression of an antigen by a cell is said to be antibody-detectable if a significantly detectable amount of antibody will bind to the antigen in a standard immunocytochemistry or flow cytometry assay, optionally after fixation of the cells, and optionally using a labeled secondary antibody.

The expression of cardiomyocyte-specific gene products can also be detected at the mRNA level by Northern blot analysis, dot-blot hybridization analysis, or by reverse transcriptase initiated polymerase chain reaction (RT-PCR) using sequence-specific primers in standard amplification methods using publicly available sequence data (GenBank®). Expression of tissue-specific markers as detected at the protein or mRNA level is considered positive if the level is at least or about 2-, 3-, 4-, 5-, 6-, 7-, 8-, or 9-fold, and more particularly more than 10-, 20-, 30, 40-, or 50-fold above that of a control cell, such as an undifferentiated pluripotent stem cell or other unrelated cell type or an immature or progenitor cell type.

Once markers have been identified on the surface of cells of the desired phenotype, including maturity state, they can be used for immunoselection to further enrich the population by techniques such as immunopanning or antibody-mediated fluorescence-activated cell sorting (FACS).

Under appropriate circumstances, pluripotent stem cell-derived cardiomyocytes often show spontaneous periodic contractile activity. This means that when they are cultured in a suitable tissue culture environment with an appropriate $Ca^{2+}$ concentration and electrolyte balance, the cells can be observed to contract across one axis of the cell, and then release from contraction, without having to add any additional components to the culture medium. The contractions are periodic, which means that they repeat on a regular or irregular basis, at a frequency between about 6 and 200 contractions per minute, and often between about 20 and about 90 contractions per minute in normal buffer. Individual cells may show spontaneous periodic contractile activity on their own, or they may show spontaneous periodic contractile activity in concert with neighboring cells in a tissue, cell aggregate, or cultured cell mass.

The contractile activity of the cells can be characterized according to the influence of culture conditions on the nature and frequency of contractions. Compounds that reduce available $Ca^{2+}$ concentration or otherwise interfere with trans-membrane transport of $Ca^{2+}$ often affect contractile activity. For example, the L-type calcium channel blocker diltiazem inhibits contractile activity in a dose-dependent manner. On the other hand, adrenoceptor agonists like isoprenaline and phenylephrine have a positive chronotropic effect. Further characterization of functional properties of the cell can involve characterizing channels for $Na^+$, $K^+$, and $Ca^{2+}$. Electrophysiology can be studied by patch clamp analysis for cardiomyocyte like action potentials.

Functional attributes provide a manner of characterizing cells and their precursors in vitro, but may not be necessary for some of the uses referred to herein. For example, a mixed cell population enriched for cells bearing some of the markers listed above, but not all of the functional or electrophysiology properties, can be of considerable therapeutic benefit if they are capable of grafting to impaired cardiac tissue, and acquiring in vivo the functional properties needed to supplement cardiac function, in certain embodiments of the invention.

IV. Examples

In certain aspects of the invention, cardiomyocytes, hepatocytes, and other cells may be derived from pluripotent stem cells in vitro.

The term "pluripotent stem cell" refers to a cell capable of giving rise to cells of all three germinal layers, that is, endoderm, mesoderm and ectoderm. Although in theory a pluripotent stem cell can differentiate into any cell of the body, the experimental determination of pluripotency is typically based on differentiation of a pluripotent cell into several cell types of each germinal layer. In some embodiments of the present invention, a pluripotent stem cell is an embryonic stem (ES) cell derived from the inner cell mass of a blastocyst. In other embodiments, the pluripotent stem cell is an induced pluripotent stem cell derived by reprogramming somatic cells. In certain embodiments, the pluripotent stem cell is an embryonic stem cell derived by somatic cell nuclear transfer.

A. Embryonic Stem Cells

Embryonic stem (ES) cells are pluripotent cells derived from the inner cell mass of a blastocyst. ES cells can be isolated by removing the outer trophectoderm layer of a developing embryo, then culturing the inner mass cells on a feeder layer of non-growing cells. Under appropriate conditions, colonies of proliferating, undifferentiated ES cells are produced. The colonies can be removed, dissociated into individual cells, then replated on a fresh feeder layer. The replated cells can continue to proliferate, producing new colonies of undifferentiated ES cells. The new colonies can then be removed, dissociated, replated again and allowed to grow. This process of "subculturing" or "passaging" undifferentiated ES cells can be repeated a number of times to produce cell lines containing undifferentiated ES cells (U.S. Pat. Nos. 5,843,780; 6,200,806; 7,029,913). A "primary cell culture" is a culture of cells directly obtained from a tissue such as the inner cell mass of a blastocyst. A "subculture" is any culture derived from the primary cell culture.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson and Marshall, 1998; Reubinoff et al, 2000.) In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel™ or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thompson et al. In addition, subclones H9.1 and H9.2 of the H9 line have been developed. It is anticipated that virtually any ES or stem cell line known in the art and may be used with the present invention, such as, e.g., those described in Yu and Thompson, 2008, which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

B. Induced Pluripotent Stem Cells

Induced pluripotent stem (iPS) cells are cells that have the characteristics of ES cells but are obtained by the reprogramming of differentiated somatic cells. Induced pluripotent stem cells have been obtained by various methods. In one method, adult human dermal fibroblasts are transfected with transcription factors Oct4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having neuronal structures and neuronal markers. It is anticipated that virtually any iPS cells or cell lines may be used with the present invention, including, e.g., those described in Yu and Thompson, 2008.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse are also known (Takahashi and Yamanaka, 2006). Induction of iPS cells typically require the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

IPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5\text{-}10 \times 10^6$ cells into the rear leg muscles of 8-12 week old male SCID mice. Teratomas develop that demonstrate at least one cell type of each of the three germ layers.

In certain aspects of the present invention, iPS cells are made from reprogramming somatic cells using reprogramming factors comprising Oct family member and a Sox family member, such as Oct4 and Sox2 in combination with Klf or Nanog as describe above. The somatic cell in the present invention may be any somatic cell that can be induced to pluripotency, such as a fibroblast, a keratinocyte, a hematopoietic cell, a mesenchymal cell, a liver cell, a stomach cell, or a β cell. In a certain aspect, T cells may also be used as source of somatic cells for reprogramming (see U.S. Application No. 61/184,546, incorporated herein by reference).

Reprogramming factors may be expressed from expression cassettes comprised in one or more vectors, such as an integrating vector or an episomal vector, such as a EBV element-based system (see U.S. application Ser. No. 12/478,154, incorporated herein by reference; Yu et al., 2009). In a further aspect, reprogramming proteins could be introduced directly into somatic cells by protein transduction (see U.S. application Ser. No. 12/723,063, incorporated herein by reference) or RNA transfection (see U.S. application Ser. No. 12/735,060).

C. Induced Pluripotent Stem Cells

Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by elec-trofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

V. Genetic Modification of Cells

In certain aspects, the cells of this invention can be made to contain one or more genetic modifications by genetic engineering of the cells either before or after differentiation (U.S. Patent Application Publication No. 2002/0168766). A cell is said to be "genetically modified" or "transgenic" when a polynucleotide has been transferred into the cell by any suitable means of artificial manipulation, or where the cell is a progeny of the originally altered cell that has inherited the polynucleotide. In some embodiments, the cells that are genetically modified are also subjected to the media methods of the present invention, although in other embodiments the cells that are genetically modified are not exposed to particular media.

In some embodiments, the genes that are transgenically expressed in the cells may be one or a combination of enzymes present in the pathways and those that regulate or augment the function of a desired pathway. Increasing aerobic respiration can be accomplished by increasing the substrates that are used in those pathways and/or upregulating the genes that encode the enzymes that directly function in aerobic respiration or support it. In some embodiments, the genetically modified cells are cultured in particular media of the invention.

In particular embodiments of the invention, the cells are genetically engineered to express 1) regulatory genes that drive the expression of metabolic enzymes from aerobic respiration pathways; 2) genes that encode pathway enzymes or co-factors; and/or 3) genes that code for proteins that transport substrates utilized in aerobic respiration pathways (such as fatty acid transporters). The cells may be also genetically engineered to express anti-oxidants and/or free radical scavengers and/or the cell media may comprise anti-oxidants and free radical scavengers.

In some embodiments, the cells are manipulated to harbor metabolic enzymes associated with such metabolic pathways as oxidative phosphorylation, fatty acid oxidation, pyruvate decarboxylation, and the Citric Acid Cycle. Exemplary fatty acid oxidation enzymes include acyl CoA dehydrogenase, enoyl CoA hydratase, L-β-hydroxyacyl CoA dehydrogenase, and β-ketothiolase; exemplary co-factors include flavin adenine dinucleotide (FAD) and nicotinamide adenine dinucleotide ($NAD^+$). Exemplary citric acid cycle enzymes include citrate synthase, aconitase, isocitrate dehydrogenase, α-ketoglutarate dehydrogenase, succinyl-CoA synthetase, succinate dehydrogenase, fumarase, and malate dehydrogenase, for example. Exemplary oxidative phosphorylation enzymes include NADH dehydrogenase, succinate dehydrogenase, electron transfer flavoprotein-ubiquinone oxidoreductase, Q-cytochrome c oxidoreductase, or cytochrome c oxidase, for example. Exemplary pyruvate decarboxylation enzymes include pyruvate dehydrogenase, dihydrolipoyl transacetylase, and dihydrolipoyl dehydrogenase, for example.

In particular embodiments of the invention, the cells are genetically engineered to express one or more of the following: fatty acid translocase (Cd36); plasma membrane associated fatty acid binding protein; fatty acid transport protein (FATP1, FATP2, FATP3, FATP4, FATP5, and/or FATP6); acyl-CoA synthetase; carnitine palmitoyl transferase 1

(CPT1); carnitine palmitoyl transferase 2 (CPT2); peroxisome proliferator-activated receptors (PPARs) alpha, beta/delta; and/or L-carnitine.

The genes could be utilized in a transgenic approach by a variety of methods. In specific embodiments, they may be expressed under the control of constitutive promoters, tissue-specific promoters, or chemically-inducible promoters (such as the commercially available dexamethasone-inducible promoter system), for example, or native dexamethasone-inducible promoters, such as NR112 (PXR), or CYP3A. The genes may be provided to cells by a variety of methods known in the art, including by plasmid, episomal, liposomal, or viral vectors (adenoviral, retroviral, adeno-associated, and so forth), homologous recombination (basic as well as enhanced by Zn finger nucleases, TALENs, meganucleases, for example), transposons (such as piggyBac, sleeping beauty, for example), and cre-lox-utilizing methods for cassette exchange.

Promoters for the genetic constructs in the cells that are active in stem cell-derived cells are useful in the invention. Exemplary promoters active in iPS or ES cell-derived cardiomyocytes include, for example, cTNT, cTNI, alpha myosin heavy chain, beta myosin heavy chain, myosin light chain 2V, and myosin light chain 2A. Exemplary promoters active in iPS or ES cell-derived hepatocytes include, for example, AFP, ALB, SERPINA1, TTR, CPS1, and/or HNF4A.

In some aspects, the cells can be processed to increase their replication potential by genetically altering the cells to express telomerase reverse transcriptase, either before or after they progress to restricted developmental lineage cells or terminally differentiated cells (U.S. Patent Application Publication No. 2003/0022367).

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are cells that are genetically altered to express one or more growth factors of various types such as FGF, cardiotropic factors such as atrial natriuretic factor, cripto, and cardiac transcription regulation factors, such as GATA-4, Nkx2.5, and MEF2-C. Production of these factors at the site of administration may facilitate adoption of the functional phenotype, enhance the beneficial effect of the administered cell, or increase proliferation or activity of host cells neighboring the treatment site.

In certain embodiments of the invention, cells containing a nucleic acid construct of the present invention may be identified in vitro or in vivo by including a marker in an expression vector, such as a selectable or screenable marker. Such markers would confer an identifiable change to the cell permitting easy identification of cells containing the expression vector, or help enrich or identify differentiated cardiac cells by using a cardiomyocyte-specific promoter, such as promoters of cardiac troponin I (cTnI), cardiac troponin T (cTnT), α-myosin heavy chain (MYH6), myosin light chain-2v (MLC-2v), GATA-4, Nkx2.5, N-cadherin, β1-adrenoceptor, the MEF-2 family of transcription factors, creatine kinase MB (CK-MB), myoglobin, or atrial natriuretic factor (ANF).

Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, blasticidin, DHFR, GPT, zeocin and histidinol are useful selectable markers.

In addition to markers conferring a phenotype that allows for the discrimination of transformants based on the implementation of conditions, other types of markers including screenable markers such as GFP, whose basis is colorimetric analysis, are also contemplated.

Examples of such screenable include genes encoding cell surface proteins (e.g., CD4, HA epitope), fluorescent proteins, antigenic determinants and enzymes (e.g., β-galactosidase). The vector containing cells may be isolated, e.g., by FACS using fluorescently-tagged antibodies to the cell surface protein or substrates that can be converted to fluorescent products by a vector encoded enzyme.

In specific embodiments, the screenable marker encodes a fluorescent protein. A broad range of fluorescent protein genetic variants have been developed that feature fluorescence emission spectral profiles spanning almost the entire visible light spectrum. Mutagenesis efforts in the original *Aequorea victoria* jellyfish green fluorescent protein have resulted in new fluorescent probes that range in color from blue to yellow, and are some of the most widely used in vivo reporter molecules in biological research. Longer wavelength fluorescent proteins, emitting in the orange and red spectral regions, have been developed from the marine anemone, *Discosoma striata*, and reef corals belonging to the class Anthozoa.

Alternatively, screenable enzymes such as chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

VI. Use of Cultured Cardiomyocytes

Certain aspects of this invention provide a method to culture cells of the cardiomyocyte lineage such that their primary form of metabolism is not glycolysis.

Certain aspects of this invention provide a means for developing a cardiac hypertrophy assay. Cardiac hypertrophy is characterized, at least in part, by the reintroduction of a fetal gene program in adult tissue. For example, the re-expression of the cardiac hormones (NPPA and NPPB) are characteristics of a hypertrophic response. Therefore, for ESC and iPSC derived cells to function in a cardiac hypertrophy assay, they need to developmentally mature in regard to the cardiac hormones. Culturing iPSC-derived cardiomyocytes in low glucose and low/no serum medium containing fatty acids of the present invention resulted in decreased expression of these cardiac hormones, which could then be induced to re-express under controlled conditions through the use of a hypertrophy inducing agonist such as endothelin 1.

Cardiomyocytes, as well as populations of cardiomyocytes including enriched or selected cardiomyocytes of any developmental, maturation or differentiation stage thereof can be used to screen for or identify cardioactive agents. In various non-limiting embodiments, a cardiomyocyte population used in a screen or identification method includes nodal, ventricular, sino-atrial or pacemaker cells, mature contractile cardiomyocytes, immature cardiomyocytes (cardioblasts), or a mixed population thereof.

Effect of cell function can be assessed using any standard assay to observe phenotype or activity of cardiomyocytes, such as marker expression, receptor binding, contractile activity, or electrophysiology—either in cell culture or in vivo. Pharmaceutical candidates can also be tested for their effect on contractile activity—such as whether they increase or decrease the extent or frequency of contraction. Where an effect is observed, the concentration of the compound can be titrated to determine the median effective dose ($ED_{50}$).

In certain aspects, cardiomyocytes cultured in the medium according to certain aspects of the invention could be used to measure functional properties of the cardiomyocytes, particularly cardiac specific electrical activity, such as beating frequency or field potential.

Detection of cardiac specific electrical activity of the cells and tissues of the present invention may be effected by monitoring the electrical activity thereof via a multielectrode array. Suitable multielectrode arrays may be obtained from Multi Channel Systems, Reutlingen, Germany. For example, the multielectrode array could be a two-dimensional orthogonal array which includes 60 or more electrodes positioned 100 µm or less apart. In certain aspects, the multielectrode array is configured to obtain data characterizing cardiac specific electrical activity with a frequency greater than a range selected from 1-25 kHz.

Monitoring electrical activity in the cells and tissues of the present invention can be used to provide many different types of important and novel information regarding electrical activity of cells and tissues of the present invention. For example, such monitoring can be used to monitor electrical activity individually at each electrode, or more advantageously, such monitoring can be used to generate electrical activity propagation maps, also termed herein "activation maps", depicting electrical activity as a function of local activation time at each electrode, for example in the form of a color-coded gradient. Such activation maps can be used to depict conduction velocity and conduction directionality of propagative electrical activity, preferably in the form of conduction velocity vectors, of electrical activity propagation over an area of the microelectrode array, In accordance with certain aspects of the invention, there are also provided methods of screening and identifying cardioactive agents. In one embodiment, a method includes contacting a cardiomyocyte with a test agent; and determining if the test agent modulates an activity or function of cardiomyocytes within the population. A test agent modulating an activity or function of cardiomyocytes within the population identifies the test agent as a cardioactive agent. Exemplary activity or function that can be modulated include contraction or beating, or production of a metabolic product (e.g., production of one or more of urea, creatine or CO2), or intracellular enzyme (e.g., one or more of lactate dehydrogenase, creatine phosphokinase (CPK), creatine kinase (CK) or troponin), or cellular apoptosis, necrosis, death; or de-differentiation, maturation, or division.

Methods of screening and identifying cardioactive agents include those suitable for high throughput screening, which include arrays of cardiomyocyte cells (e.g., microarrays) positioned or placed, optionally at pre-determined locations or addresses. High-throughput robotic or manual handling methods can probe chemical interactions and determine levels of expression of many genes in a short period of time. Techniques have been developed that utilize molecular signals (e.g., fluorophores) and automated analyses that process information at a very rapid rate (see, e.g., Pinhasov et al., 2004). For example, microarray technology has been extensively utilized to probe the interactions of thousands of genes at once, while providing information for specific genes (see, e.g., Mocellin and Rossi, 2007).

Such high-throughput screening methods can identify cardioactive agents. For example, cardiomyocyte cells (e.g., cardiomyoblasts, cardiomyocytes or sino-atrial nodal cells) can be positioned or placed (pre-seeded) on a culture dish, tube, flask, roller bottle or plate (e.g., a single multi-well plate or dish such as an 8, 16, 32, 64, 96, 384 and 1536 multi-well plate or dish), optionally at defined locations, for identification of potentially therapeutic molecules. Libraries that can be screened include, for example, small molecule libraries, siRNA libraries, and adenoviral transfection vectors.

Such high throughput methods are therefore also applicable to predictive toxicology. The use of cardiomyocyte cells (e.g., cardiomyoblasts, cardiomyocytes or sino-atrial nodal cells) positioned or placed (pre-seeded) on a culture dish, tube, flask, roller bottle or plate (e.g., a single multi-well plate or dish such as an 8, 16, 32, 64, 96, 384 and 1536 multi-well plate or dish), optionally at defined locations, for high-throughput or high content screening using small molecule libraries, siRNA libraries, adenoviral transfection vectors, and gene based microarray approaches can identify various therapeutic and cardiac liability targets. Such techniques also allow direct high-throughput measurement of cardiac intervention strategies by means of fluorescent reporter dyes and biomarkers for cell health and morphological phenotype, expression of fluorescent reporter proteins, various FRET approaches and direct measurement of electrophysiological currents in live cells.

In certain embodiments, cardiomyocytes prepared by at least certain methods of the invention can be used commercially to screen for factors (such as solvents, small molecule drugs, peptides, oligonucleotides) or environmental conditions (such as culture conditions or manipulation) that affect the characteristics of such cells and their various progeny, such as beating frequency or beating rate oscillations. The culture medium as described above may increase beating frequency and reduce the incidence of beating rate oscillations, thereby increasing the stability of beating frequency recordings.

In certain aspects, the cardiomyocytes could be cultured in the medium as described above to facilitate a) normal beating frequency of cardiomyocytes; b) normal field potential duration of beating cardiomyocytes; c) beating frequency of cardiomyocytes treated with compounds that may affect beating frequency; or d) field potential duration of cardiomyocytes treated with compounds that may affect field potential duration.

Beating (contractile) frequency of cardiomyocytes can be modulated by culture media pH, temperature, or a modulator drug. Exemplary non-limiting modulator drugs include catecholamine, a calcium channel blocker, or potassium.

VII. Kits of the Invention

Any of the compositions described herein may be comprised in a kit, including, for example, one or more media reagents, cells in need of metabolic maturation (including stem cells), polynucleotides, peptides, transfection reagents or vehicles, a combination thereof, and so forth.

The kits may comprise a suitably aliquoted composition of the present invention. The components of the kits may be packaged either in aqueous media or in lyophilized form, where appropriate. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the kit component(s) in close confinement for commercial sale. Such containers may include injection or blow molded plastic containers into which the desired vials are retained.

However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

SF8 Medium Improved ET-1 BNP Response of iPSC-Derived Cardiomyocytes

Cellular assays of cardiac hypertrophy will require hESC and hiPSC-derived cardiomyocytes to be metabolically mature, such as by utilizing FAO. During a cardiac stress response, including cardiac hypertrophy, the preferred energy source switches back to the so called "fetal program", glycolysis. In addition, mice with a cardiomyocyte specific conditional knockout of key regulators of the FAO metabolism pathway demonstrate a chronic hypertrophic state (Cheng et al., 2004). Human ES cell and iPS cell-derived cardiomyocytes are thought to represent a 'fetal' or 'immature' stage of development (He et al., 2003). Included in the 'fetal' gene program of cardiomyocytes are genes that are also associated with the hypertrophic response, such as NPPA and NPPB. Therefore, in aspects of the invention these cells utilize glycolysis for metabolism. For certain aspects of the invention, in order to reduce the basal 'stressed' or 'hypertrophic' state of cultured stem cell-derived cardiomyocytes, it is useful to adapt the metabolism from primarily glycolysis to primarily FAO.

In embodiments of the invention, the endothelin-induced BNP response of iPSC-derived cardiomyocytes (CMs) requires an increased maturation state of the CMs. One manifestation of an increased maturation state is a decrease in the uninduced expression of cardiac hormones, including BNP. The inventors generated a serum free, glucose free medium with fatty acids (termed SF8) to increase the metabolic maturation state of the CMs. In experiment 1, SF8 medium was evaluated for its ability to upregulate genes associated with fatty acid oxidation (CPT1 and PPARa) and decrease certain cardiac hormone genes associated with fetal heart cells and cardiac hypertrophy (such as NPPA and NPPB). In this experiment, cell numbers, purity (cTNT) and viability were compared with cells cultured in standard maintenance medium (iCMM: glucose-free/pyruvate free DMEM, 10 mM galactose, 1 mM Na pyruvate, 10% dialyzed serum). In experiments 2, 3 and 4 cells cultured in SF8 media were compared to typical hypertrophy culture conditions (DMEM: M199) for their ability to upregulate BNP in response to ET-1.

EXPERIMENTAL DESIGN

Exemplary Media for Studies

DMEM:M199 (Control)

| | |
|---|---|
| DMEM + GlutaMax ™ (with glucose and pyruvate) | 3 parts |
| Medium199 | 1 part |

SF8

| | |
|---|---|
| DMEM (no glucose, no pyruvate) | |
| L-carnitine | 2 mM |
| Creatine | 5 mM |
| Taurine | 5 mM |
| Non-Essential Amino Acids | 1 mM |
| L-glutamine + BME (or L-glutamine only) | 2 mM |
| ITS-A | 1x |
| Linoleic-Oleic acid (or Linoleic acid only) | 1x |

* Note: ITS-A contains 0.11 g/L sodium pyruvate in a 1x stock: obtained from Life Technologies (Cat No. 51300). Fatty Acids also contain 1 mg/mL BSA in a 1x stock. Linoleic-oleic acid obtained from Sigma-Aldrich (L9655) and at 1x each are present at a concentration of 9.4 ug/mL. Linoleic acid only was obtained from Sigma-Aldrich (L9530) and at 1x is present at a concentration of 9.4 ug/mL.

Protocols

Experiment 1

Figure 1B:
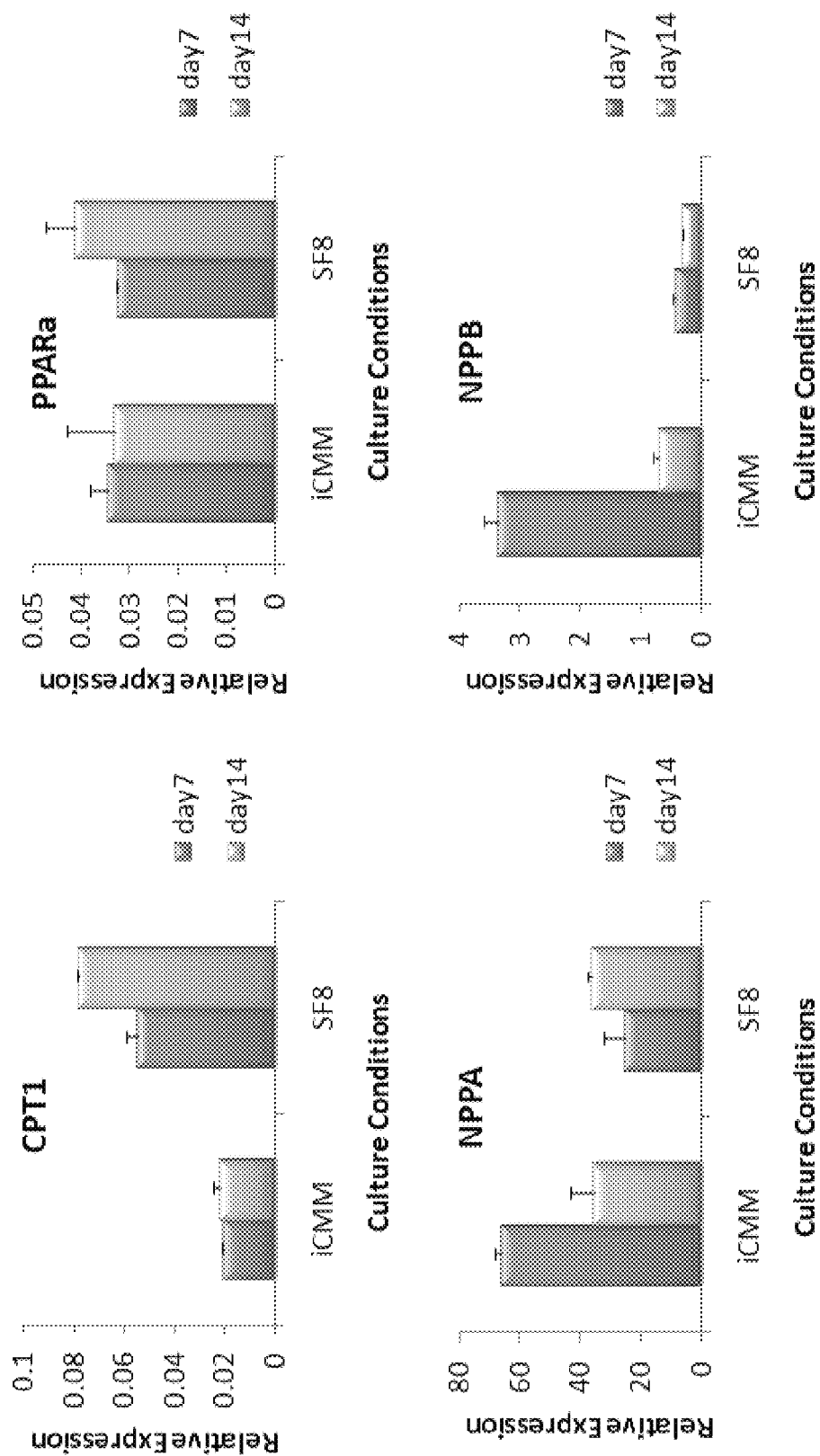

FIG. 1a is a flow chart schematic of the cell culture studies of experiment 1. FIG. 1b shows iPSC-derived CMs cultured in SF8 upregulate CPT-1 and down-regulated NPPB. At both day 7 and day 14 of cell culture iPSC-derived CMs displayed a significant increase in CPT-1 expression, however no effect was detected in expression of PPARa. At day 7 of culture, NPPA expression was lower in SF8 than iCMM but the levels were similar by day 14. NPPB expression was lower at both day 7 and 14 in SF8 compared to iCMM.

Figure 2:
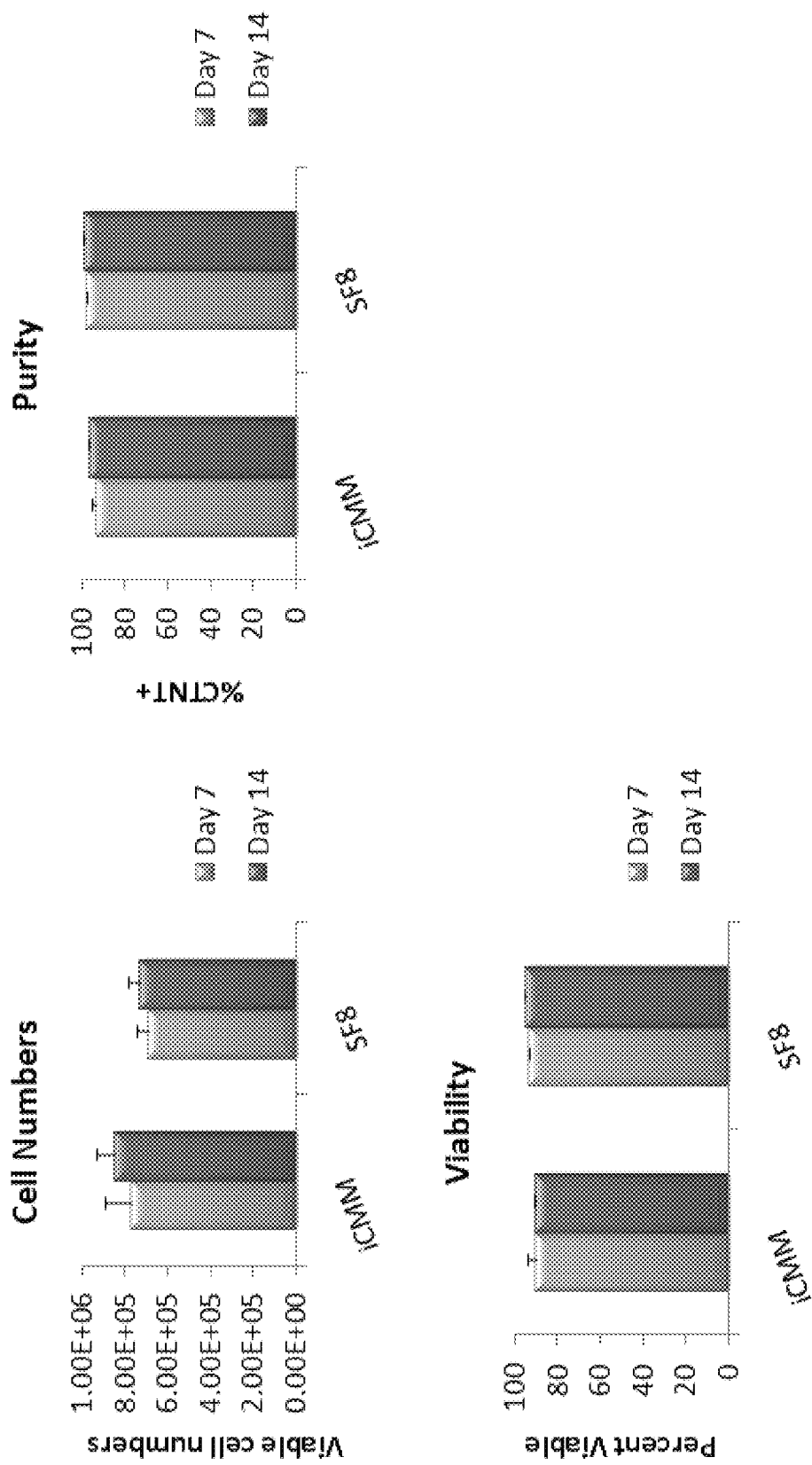
FIG. 2: Cell numbers, purity and viability are maintained in SF8 medium.

FIG. 2: Cell numbers, purity and viability are maintained in SF8 medium. When measured at days 7 and 14, cell numbers, purity (cTNT %) and viability are comparable between iCMM and SF8.

Experiment 2, 3, 4

Figure 3A:
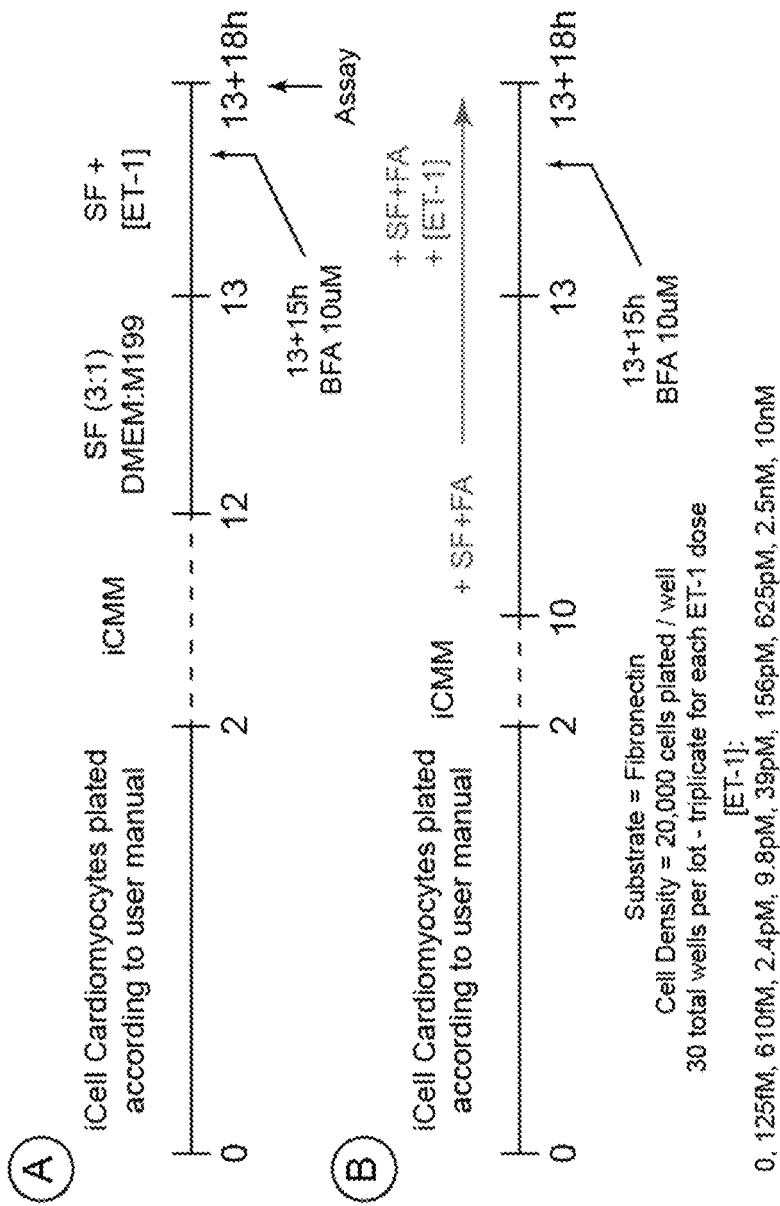
FIG. 3a-b: (a), A flow chart schematic of the cell culture studies with iPSC-derived cardiomyocytes (see Experiments 2, 3, and 4, below). (b), Example of Flow Cytometry Data using exemplary methods of the invention.
Figure 3B:
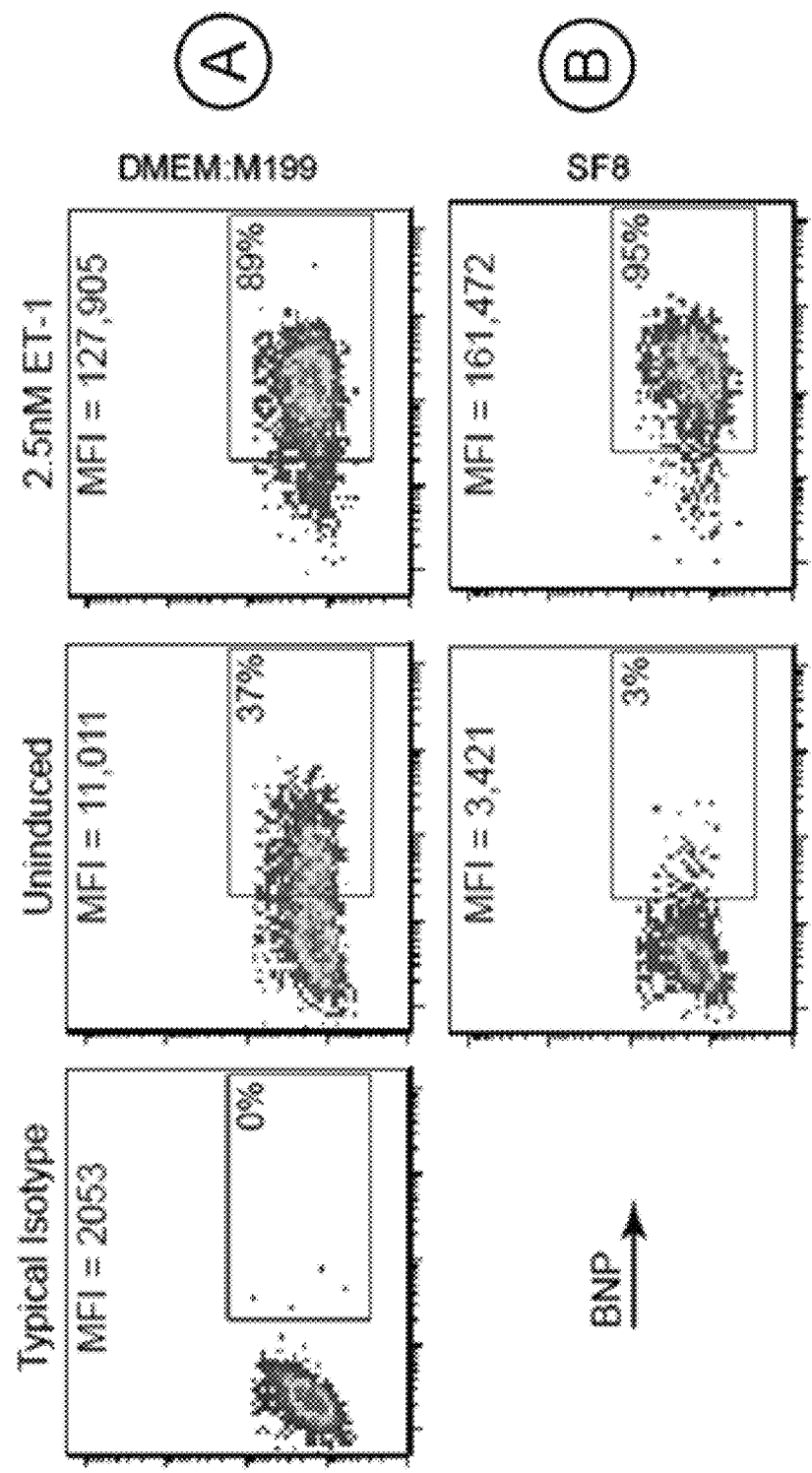

FIG. 3a is a flow chart schematic of the cell culture studies used in the experiments. FIG. 3b provides examples of Flow Cytometry Data using protocol A, or protocol B as graphically shown above. All wells were harvested and then stained with Live/Dead Viability Assay (Invitrogen). Cells were then fixed and permeabilized with saponin. A small sample of cells from each well was pooled for isotype controls. Cells were stained using mouse-α-pro-BNP (clone 15F11) (Abcam) or mouse IgG2b isotype control, in the presence of saponin. Cells were then washed and incubated with dnk-a-mouse IgG-Alexa-647 (H+L) (Invitrogen), in the presence of saponin. Cells were then washed and analyzed on an Acuri Flow Cytometer. Live cells were gated and the Median Fluorescence Intensity (MFI) of Alexa-647 of all live cells was calculated.

Figure 4:
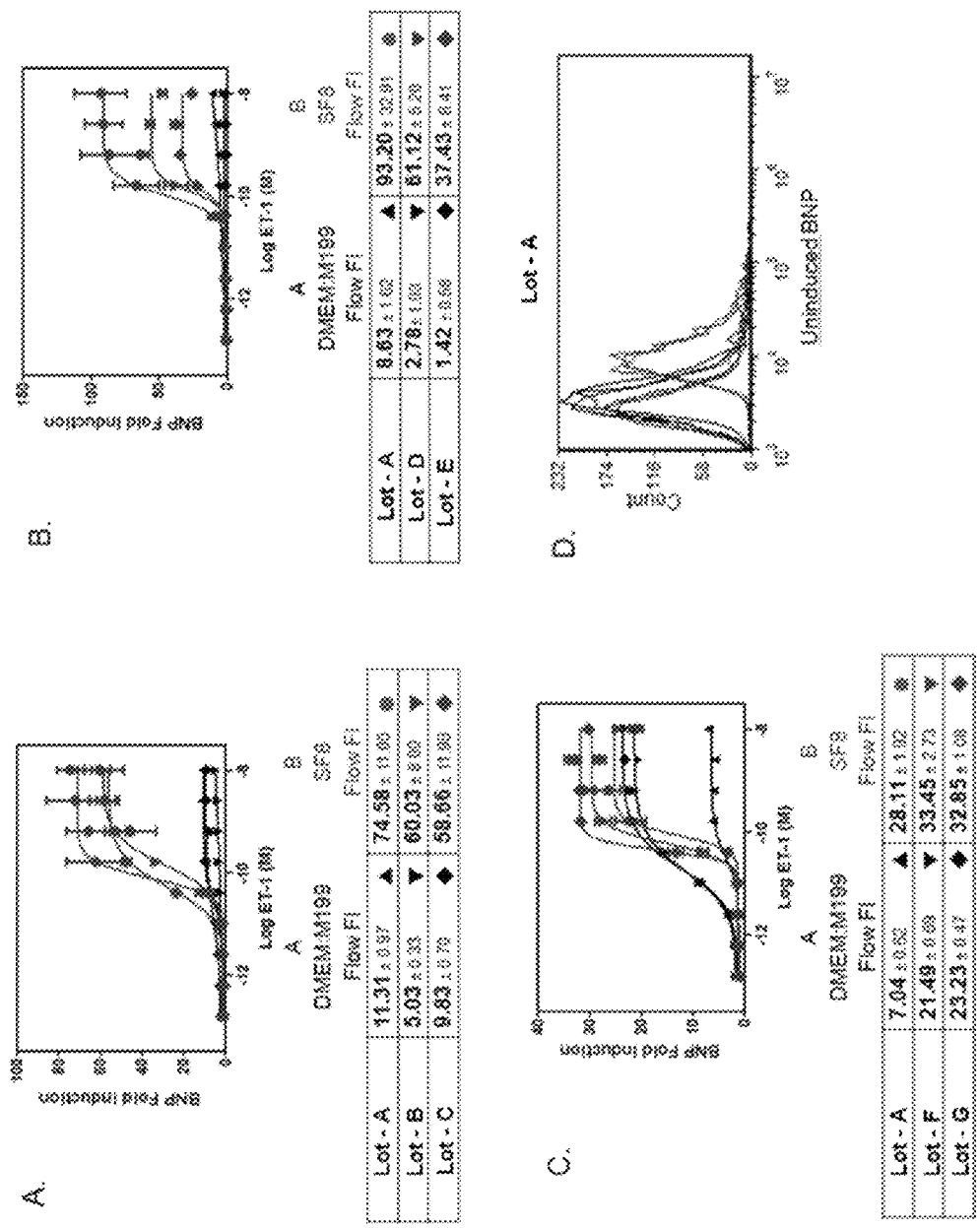
FIG. 4: Cell Culture and endothelin (ET-1) induction in SF8 medium improves functional response of CMs.

FIG. 4 shows that cell culture and ET-1 induction in SF8 medium improves functional response of CMs. CMs were thawed, cultured and assayed in 3 independent experiments (A, B, C). Cell lot A was used as an internal control for each experiment. The fold induction was calculated as the maximum MFI divided by the uninduced MFI for each cell lot. For Cell lot #s A, B, C, D, and E, the culture with SF8 medium clearly improved the functional response of the CMs. Lot #s F and G had only a moderate improvement in their fold induction, likely owing to the fact that their functional response was nearly maximal in the DMEM:M199 culture. All the SF8 Fold inductions for the third experiment (C) are likely lower than the first and second experiments because the uninduced BNP expression was slightly higher on that day (D). The increase in the uninduced MFI decreases the overall fold induction. However, lot A still displayed a significant improvement in response when cultured in SF8 medium.

iPSC-derived CM cultured in SF media containing fatty acids and without glucose showed signs of CM maturation including increased CPT1 expression and decreased cardiac hormone expression (NPPA and NPPB). PPARa expression did not change in either culture. This could be the result of robust expression of this gene without the addition of fatty acids. Culture in SF8 medium did not result in changes in cell number, viability or purity.

Different lots of iPSC-derived CMs display variability in their response to ET-1 as measured by BNP expression, when cultured in the typical "hypertrophy SF medium" (DMEM: M199). Some lot numbers fail to generate >5 fold response over uninduced cells. Culture in SF8 medium resulted in increased responsiveness to ET-1 in all CM lots tested. This increased responsiveness is due, at least in part, to the decreased uninduced expression of BNP compared to typical culture.

Example 2

Examples of Cardiomyocyte and Hepatocyte Functional Assays Dependent on Metabolic Maturation of Cells Upon conversion of stem cell-derived cells from an immature state to a metabolically mature state, such as away from glycolysis to utilizing aerobic respiration, the resultant cells may be utilized for a variety of purposes that benefit from the altered form of metabolism. In Example 1, such an example was provided in which iPSC-derived cardiomyocytes matured in SF8 medium were utilized in a cardiac hypertrophy assay. Other exemplary cases are described below.

In cardiomyocytes, mitochondrial function is critical for viability through ATP synthesis, ion homeostasis, and the regulation of apoptosis and necrosis (Gustafsson and Gottlieb, 2008). For these reasons mitochondria are clearly a useful toxicological target. Mitochondrial toxicity is linked to many of the drugs receiving Black Box Warnings from the FDA, and at least three drugs have been pulled from the market because of organ toxicity directly related to collapse of the mitochondrial membrane potential (Dykens and Will, 2007). Therefore, in order to utilize hESC or hiPSC-derived cardiomyocytes to screen for mitochondrial toxicity, it is useful to promote reliance on mitochondria and aerobic respiration.

Cellular Assays of Hepatic Steatosis:

Cellular assays of steatosis will require hESC and hiPSC-derived hepatocytes to utilize OXPHOS. It is known that defects in mitochondrial OXPHOS can lead to steatosis. Thus far, ES-derived hepatocytes have been shown to primarily utilize glycolysis (Sharma et al., 2008) instead of OXPHOS, giving impetus to their immature or "hepatocyte-like" reputation. For example, mice with a hepatocyte specific-conditional knockout of COX10, a key regulator of OXPHOS, display a steatotic phenotype (Diaz et al., 2008). Therefore, in order to identify targets of drug-induced hepatic steatosis it is useful that stem cell-derived hepatocytes be capable of OXPHOS.

heSC or hiPSC-Derived Hepatotoxicity Assays:

Mitochondrial biogenesis is a critical part of hepatocyte maturation. It is likely that increased mitochondrial mass during hepatocyte differentiation and maturation is linked to the switch from glycolysis to OXPHOS. Drugs withdrawn from the market often are due to hepatotoxicity caused by the production of toxic intermediates resulting in reduced OXPHOS and ATP levels. Therefore there is a means for increasing the maturity state of stem cell-derived hepatocytes is to culture them in medium that promotes the proliferation of mitochondria capable of OXPHOS. Total mitochondria and changes in polarity can be assessed using the FLOW based assays Mitotracker green in combination with Mitotracker red, respectively.

Thus, to achieve these exemplary tasks with stem-cell derived cells, such as hES and iPS cell-derived cells, one exposes the cells to conditions to decrease glycolysis and adapt to aerobic metabolism. The stem cell-derived cell types are cultured in conditions including one or more of the following: 1) containing high concentrations of free fatty acids, 2) containing low to no glucose or (optionally) pyruvate, 3) containing molecules that induce the expression of genes associated with the FAO metabolism pathway (Cheng et al., 2004), 4) containing L-carnitine, 5) addition of anti-oxidants (such as ascorbic acid), 6) combinations of any of those conditions. Following induction of FAO metabolism, and the reduced expression of genes associated with "fetal" state, the cells are then assessed for enhanced metabolic maturity using functional assays and by assessing gene expression associated with mature cells, all as detailed herein.

Lactate Dehydrogenase Activity Assay:

Stem cell-derived tissues, such as iPSC-derived cardiomyocytes, are well documented to display fetal or immature characteristics in comparison to adult tissues. Postnatal maturation of the heart is associated with significant changes in energy metabolism. Fetal hearts primarily utilize anaerobic glycolysis, while the adult heart utilizes primarily aerobic metabolism, with free fatty acids as the predominant substrate.

Lactate dehydrogenase (LDH) is an enzyme that catalyzes the interconversion of lactate and pyruvate. It consists of four subunits which combine to form five different isoenzymes. Enzymatic activity of the isozymes LDH4 and LDH5 are indicative of anaerobic metabolism, while that of isozymes LDH1 and LDH2 are indicative of aerobic metabolism. Consistent with these activity levels and of maturation of the metabolic pathways during development, LDH4 and LDH5 activity are predominant in the fetal heart, while LDH1 and LDH2 activity are predominant in the adult heart (Fischer et al., 2010).

iPSC-derived cardiomyocytes (iCell Cardiomyocytes) were cultured in iCMM or SF8 according to the protocol used to culture cells in FIG. 1, with the following modifications: a) 96-well format, b) 20,000 plateable cells per well, and c) only Linoleic acid was used in the SF8 medium as opposed to Linoleic-Oleic acid. Following cell lysis with CelLytic reagent (Sigma C2978) the cells were incubated for 15 minutes on ice and 2 uL of lysate was analyzed using the Helena Laboratories QuickGel system (1284) and QuickGel LD Isoenzyme Kit (3538T) as per the manufacturer instructions.

Figure 5:
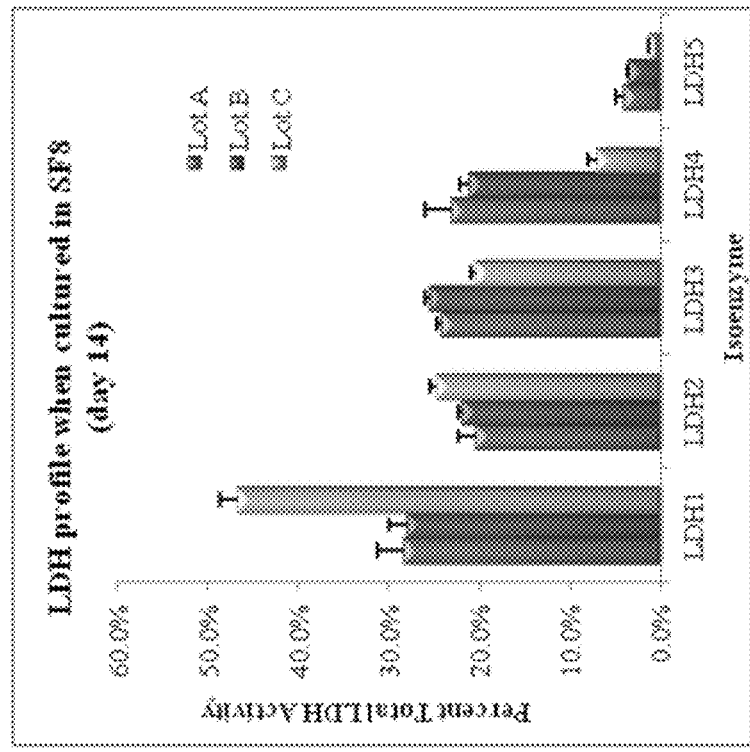
FIG. 5: Lactate dehydrogenase activity profile when iPSC-derived cardiomyocytes are cultured in (a) iCMM or (b) SF8 media.
Figure 5:
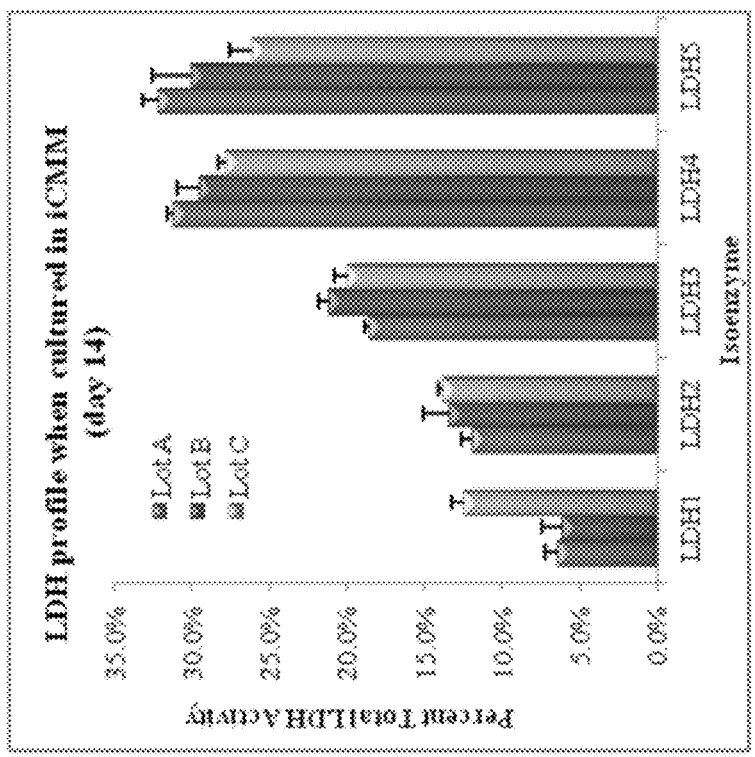

The percent of total LDH activity was calculated using Image J software. Three total wells from each lot of cells were analyzed 14 days after plating for their LDH1-5 activity profiles (FIG. 5). Consistent with a fetal or immature developmental state, cells cultured in iCMM displayed predominantly LDH4 and LDH5 activity with low LDH1 and LDH2 activity. In contrast, cells cultured in SF8 medium displayed predominantly LDH1 and LDH2 activity with low LDH4 and LDH5 activity. FIG. 5 shows LDH activity levels of cardiomyocytes when cultured in iCMM or SF8 media, according to protocol in FIG. 1, with the following modifications: a) 96-well format, b) 20,000 plateable cells per well, c) Linoleic acid was used in the SF8 medium as opposed to Linoleic-Oleic acid. Following cell lysis with CelLytic reagent (Sigma C2978) for 15 minutes on ice, 2 uL of lysate was analyzed using Helena Laboratories QuickGel system (1284) and QuickGel LD Isoenzyme Kit (3538T) as per manufacturer instructions. The percent of total LDH activity was calculated using Image J software. Three total wells from each lot were analyzed after 14 days of culture.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

Patents and Patent Applications

U.S. application Ser. No. 12/478,154
U.S. application Ser. No. 12/723,063
U.S. application Ser. No. 12/735,060
U.S. Application No. 61/184,546
U.S. Pat. No. 5,843,780
U.S. Pat. No. 6,200,806
U.S. Pat. No. 6,833,269
U.S. Pat. No. 7,029,913
U.S. Patent Application Publication No. 2002/0168766
U.S. Patent Application Publication No. 2003/0022367
U.S. Patent Application Publication No. 2011/0097799

Publications

Amit et al., *Dev. Bio.*, 227:271-278, 2000.
Andrews et al., In: *Teratocarcinomas and Embryonic Stem Cells*, Robertson (Ed.), IRL Press, 207-246, 1987.
Byrne et al., *Nature*, 450(7169):497-502, 2007.
Cheng et al., *Biochem. Biophys. Res. Commun.*, 313:(2):277-286, 2004.
Cheng et al., *Nat. Med.*, 10(11):1245-1250, 2004.
Diaz et al., *Gut*, 57(2):232-242, 2008.
Dykens and Will, *Drug Discov. Today*, 12(17-18):777-785, 2007.
Fischer et al., *BMC Dev. Biol.*, 10:70, 2010.
Gustafsson and Gottlieb, *Cardiovasc. Res.*, 77(2):334-343, 2008.
He et al., *Circ. Res.*, 93(1):32-39, 2003.
Klimanskaya et al., *Lancet.*, 365(9471):1636-1641, 2005.
Lehman and Kelly, *Clin. Exp. Pharmacol. Physiol.*, 29(4):339-345, 2002.
Lopaschuk and Jaswal, *J. Cardiovasc. Pharmacol.*, 56(2):130-140, 2010.
Mocellin and Rossi, *Adv. Exp. Med. Biol.*, 593:19-30, 2007.
Pinhasov et al., *Comb Chem High Throughput Screen*, 7(2):133-40, 2004.
Reubinoff et al., *Nat. Biotechnol.*, 18:399-404, 2000.
Sharma et al., *Cell Transplant.*, 17(3):313-323, 2008
Smith, In: Origins and Properties of Mouse Embryonic Stem Cells, Annu Rev. Cell. Dev. Biol., 2000. Takahashi and Yamanaka, *Cell.*, 126(4):663-676, 2006.
Takahashi et al., *Cell*, 131:861-872, 2007.
Thomson and Marshall, *Curr. Top. Dev. Biol.*, 38:133-165, 1998.
Thomson and Odorico, *J. Trends. Biotechnol.*, 18:53 B57, 2000.
Thomson et al. *Proc. Natl. Acad. Sci. USA*, 92:7844-7848, 1995.
Xu et al., *Nat. Biotechnol.*, 19(10):971-974, 2001.
Ying et al., *Cell*, 115:281-292, 2003.
Yu and Thompson, *Genes Dev.* 22(15):1987-97, 2008.
Yu et al., *Science*, 318:1917, 2007.
Yu et al., *Science*, 324:797-801, 2009.
Zahabi and Deschepper, *J. of Lipid Research*, 42:1325-1330, 2001.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of maturing human induced pluripotent cell-derived (human iPS-derived) cells, comprising obtaining immature, human differentiated cells that have been prepared in vitro from human iPS cells and exposing the immature, human differentiated iPS cell-derived cells to a defined media that is essentially glucose-free, essentially serum-free, and which comprises one or more fatty acids, to mature the immature, human differentiated iPS cell-derived cells to a more mature state.

2. The method of claim 1, wherein the defined media comprises one or more of the following components:
a) creatine;
b) L-carnitine;
c) taurine;
d) L-glutamine;
e) ITS-A; and
f) non-essential amino acids.

3. The method of claim 2, wherein the defined media comprises one or more of pyruvate, beta-mercaptoethanol or oleic acid.

4. The method of claim 1, wherein the media further comprises one or more anti-oxidants.

5. The method of claim 4, wherein the anti-oxidant is selected from the group consisting of vitamin A, beta-carotene, vitamins C and E, selenium, and melatonin.

6. The method of claim 1, wherein the media further comprises one or more free radical scavengers.

7. The method of claim 6, wherein the free radical scavenger is selected from the group consisting of ascorbic acid, vitamin E, and β-carotene.

8. The method of claim 1, wherein the iPS cell-derived cells are hepatocytes or cardiomyocytes.

9. The method of claim 1, wherein the cells are genetically modified.

10. The method of claim 9, wherein the cells are genetically modified to enhance expression of one or more aerobic respiration enzymes, enhance the availability of one or more aerobic respiration substrates, and/or to enhance expression of proteins that regulate or augment the function or expression of one or more aerobic respiration enzymes.

11. The method of claim 10, wherein the cells are genetically modified to increase expression of one or more proteins selected from the group consisting of fatty acid translocase (Cd36), plasma membrane associated fatty acid binding protein, fatty acid transport protein (FATP1, FATP2, FATP3, FATP4, FATP5, and/or FATP6), acyl-CoA synthetase, carnitine palmitoyl transferase 1 (CPT1), carnitine palmitoyl transferase 2 (CPT2), peroxisome proliferator-activated receptor (PPAR) alpha, PPARbeta, and PPARdelta.

12. The method of claim 9, wherein the cells are genetically modified to express an enzyme selected from the group consisting of catalase, superoxide dismutase, peroxidase, methionine reductase, glutahione peroxidase, and a combination thereof.

13. The method of claim 1, wherein the exposing step is further defined as genetically modifying the stem cell-derived cells.

14. The method of claim 13, wherein the cells are genetically modified to enhance expression of one or more aerobic respiration enzymes, one or more aerobic respiration substrates, and/or to enhance expression of proteins that regulate or augment the function or expression of one or more aerobic respiration enzymes.

15. The method of claim 14, wherein the one or more aerobic respiration enzymes is selected from the group consisting of fatty acid translocase (Cd36), plasma membrane associated fatty acid binding protein, fatty acid transport protein (FATP1, FATP2, FATP3, FATP4, FATP5, and/or FATP6), acyl-CoA synthetase, carnitine palmitoyl transferase 1 (CPT1), carnitine palmitoyl transferase 2 (CPT2), peroxisome proliferator-activated receptor (PPAR) alpha, PPARbeta, and PPARdelta.

16. The method of claim 13, wherein the cells are genetically modified to express an enzyme selected from the group consisting of catalase, superoxide dismutase, peroxidase, methionine reductase, glutahione peroxidase, and a combination thereof.

17. The method of claim 1, wherein the immature, human differentiated iPS cell-derived cells are cultured in the media for at least four days.

18. The method of claim 1, wherein following the exposing step the method further comprises assaying the immature, human differentiated iPS cell-derived cells for one or more characteristics.

19. The method of claim 18, wherein the one or more characteristics being measured requires or is enhanced by the metabolic maturity state of the cells.

20. The method of claim 18, wherein the one or more characteristics comprises expression of one or more genes or response in a cellular functional assay.

21. The method of claim 20, wherein the gene is selected from the group consisting of CPT1, PPARa, NPPA, and NPPB.

22. A method of improving the metabolic maturity state of immature, human differentiated iPS cell-derived cells, comprising obtaining immature, human differentiated cells that have been prepared in vitro from iPS cells and exposing the iPS cell-derived cells to conditions to convert the metabolism of the cells from glycolysis to aerobic respiration, to mature the immature, human differentiated iPS cell-derived cells to a more mature state.

23. The method of claim 22, wherein the exposing step is further defined as culturing the cells in a defined media that is essentially glucose-free, essentially serum-free, and which comprises one or more fatty acids.

24. The method of claim 23, wherein the defined media has one or more of the following characteristics:
    a) creatine;
    b) L-carnitine;
    c) taurine;
    d) L-glutamine;
    e) ITS-A; and
    f) non-essential amino acids.

* * * * *